United States Patent
Luxton et al.

(10) Patent No.: US 12,188,933 B2
(45) Date of Patent: Jan. 7, 2025

(54) TOOLS FOR DETECTING COCOA SWOLLEN SHOOT VIRUS COAT PROTEIN ANTIGEN

(71) Applicant: University of the West of England, Bristol, Bristol (GB)

(72) Inventors: Richard Luxton, Bristol (GB); Janice Kiely, Bristol (GB); Joel Allainguillaume, Bristol (GB); Jacqueline Mary Barnett, Bristol (GB)

(73) Assignee: University of the West of England, Bristol, Bristol (GB)

( * ) Notice: Subject to any disclaimer, the term of this patent is extended or adjusted under 35 U.S.C. 154(b) by 924 days.

(21) Appl. No.: 17/289,850

(22) PCT Filed: Oct. 29, 2019

(86) PCT No.: PCT/GB2019/053056
§ 371 (c)(1),
(2) Date: Apr. 29, 2021

(87) PCT Pub. No.: WO2020/089607
PCT Pub. Date: May 7, 2020

(65) Prior Publication Data
US 2021/0405050 A1   Dec. 30, 2021

(30) Foreign Application Priority Data

Oct. 30, 2018  (GB) ...................................... 1817721
Jun. 11, 2019  (GB) ...................................... 1908311

(51) Int. Cl.
*G01N 33/569*  (2006.01)
*G01N 33/543*  (2006.01)

(52) U.S. Cl.
CPC .  *G01N 33/56983* (2013.01); *G01N 33/54366* (2013.01); *G01N 2333/01* (2013.01)

(58) Field of Classification Search
None
See application file for complete search history.

(56) References Cited

U.S. PATENT DOCUMENTS

2021/0405050 A1*  12/2021  Luxton ............ G01N 33/54366

FOREIGN PATENT DOCUMENTS

| EP | 2278334 A1 | 1/2011 |
| WO | WO-199506252 A1 | 3/1995 |
| WO | WO 2015/139784 | * 9/2015 |

OTHER PUBLICATIONS

Alignment of SEQ 2 with UniProt db access No. A0A3Q9VXSO_9VIRU submitted Mar. 2018.*

(Continued)

*Primary Examiner* — Shanon A. Foley
(74) *Attorney, Agent, or Firm* — Morrison & Foerster LLP

(57) ABSTRACT

The present invention provides an isolated binding reagent that specifically binds to a recombinant Cocoa Swollen Shoot Virus (CSSV) coat protein antigen having at least 80% sequence identity to the amino acid sequence of SEQ ID NO: 2 or

(56) References Cited

OTHER PUBLICATIONS

Alignment of SEQ 4 with UniProt db access No. A0A3Q9VXSO_9VIRU submitted Mar. 2018.*
Kashmiri et al. (Methods. 2005; 36:25-34).*
Tamura et al. (Journal of Immunology. 2000; 164:1432-1441).*
Chingandu et al. (Virology Journal. 2017; 14: 199).*
Jacquot et al., (1999). "In situ localization of cacao swollen shoot virus in agroinfected Theobroma cacao," Arch Virol, 144:259-271.
Barnett et al., (2019). "Rapid and cost-effective 'on-site' detection of cacao swollen-shoot virus (CSSV)," available online at <https://www.icco.org/about-us/international-cocoaagreements/doc_download/3515-rapid-and-cost-effective-on-sitedetection-of-cacao-swollen-shoot-virus-cssv.html>, Accessed Feb. 25, 2019, 3 pages.
Chingandu et al., (2017). "The proposed new species, cacao red vein virus, and three previously recognized badnavirus species are associated with cacao swollen shoot disease," Virology Journal, 14:199, 14 pages.
Combined Search Report and Examination Report for United Kingdom Application No. GB1817721.2 mailed on Nov. 27, 2018, 8 pages.
Dzahini-Obiatey et al., (2010). "Early signs of infection in Cacao swollen shoot virus (CSSV) inoculated cocoa seeds and the discovery of the cotyledons of the resultant plants as rich sources of CSSV," African Journal of Biotechnology, 9(5):593-603.
Fernandez-Jaramillo et al., (2012). "Instrumentation in Developing Chlorophyll Fluorescence Biosensing: a Review," Sensors, 12:11853-11869.
Hoffmann et al., (1997). "Immunocapture polymerase chain reaction for the detection and characterization of cacao swollen shoot virus 1A isolates," Journal of Phytopathology, 145:205-212.
Hoffmann et al., (1999). "Production, characterization and application of monoclonal antibodies to the cacao swollen shoot virus isolate OA," Journal of Phytopathology, 147:725-735.
International Search Report and Written Opinion for International Application No. PCT/GB2019/053056 mailed on Jan. 27, 2020, 15 pages.
Kreisig et al., (2014). "His-tag protein monitoring by a fast mix-and-measure immunoassay," Scientific Reports, 4:5613, 5 pages.
Muller et al., (2005). "Molecular variability analysis of five new complete cacao swollen shoot virus genomic sequences," Archives of Virology, 150:53-66.
Muller et al., (2018). "Next generation sequencing elucidates cacao badnavirus diversity and reveals the existence of more than ten viral species," Virus Res., 244:235-251.
NanoComposix, (2017). "Diagnosing diseases with novel nanoparticles," Available online at <https://nanocomposix.com/pages/introduction-tolateral-flow-rapid-test-diagnostics>, Accessed Feb. 25, 2019, 1 page.
Oro et al., (2012). "Geographical differentiation of the molecular diversity of Cacao swollen shoot virus in Togo," Arch Virol., 157:509-514.
Sagemann et al., (1985). "Detection and Comparison of some Ghanaian Isolates of Cacao Swollen Shoot Virus (CSSV) by Enzyme-Linked Immunosorbent Assay (ELISA) and Immunoelectron Microscopy (IEM) Using an Antiserum to CSSV Strain IA," pp. 79-89.
Search Report and Examination Report for United Kingdom Application No. GB1817721.2 mailed on Feb. 28, 2019, 5 pages.
Tatineni et al., (2013). "Immunodetection of Triticum mosaic virus by DAS- and DAC-ELISA using antibodies produced against coat protein expressed in *Escherichia coli*: Potential for high-throughput diagnostic methods," Journal of Virological Methods, 189(1):196-203.
Wakeham et al., (2016). "Field Evaluation of a Competitive Lateral-Flow Assay for Detection of Alternaria brassicae in Vegetable *Brassica* Crops," Plant Disease, 100(9):1831-1839.
Muller et al., (2001). "Early detection of cacao swollen shoot virus using the polymerase chain reaction," Journal of Virological Methods, 93:15-22.

* cited by examiner

Fig. 2
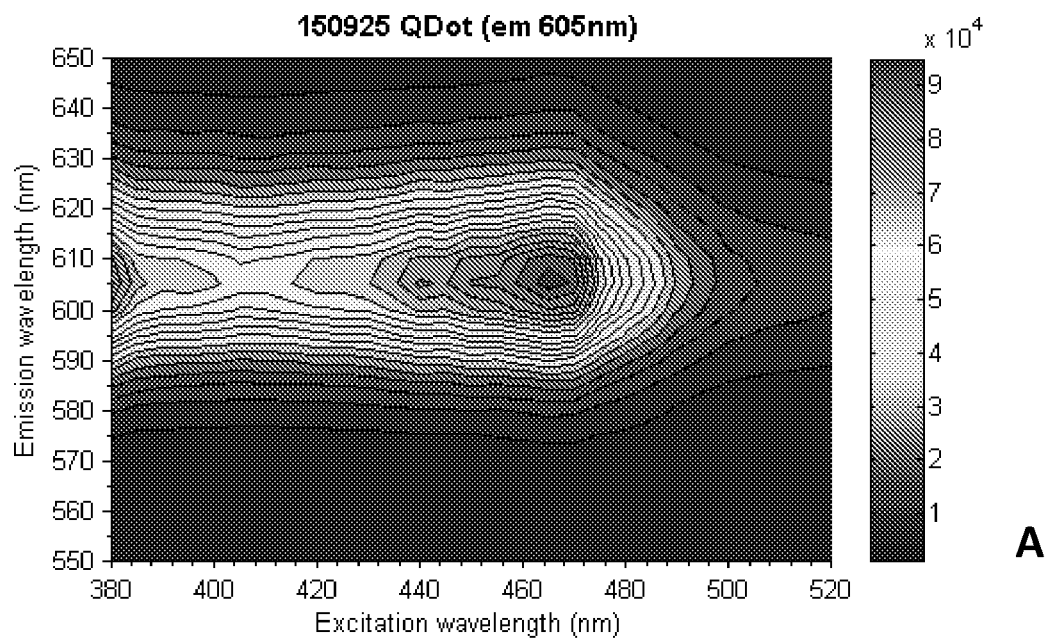
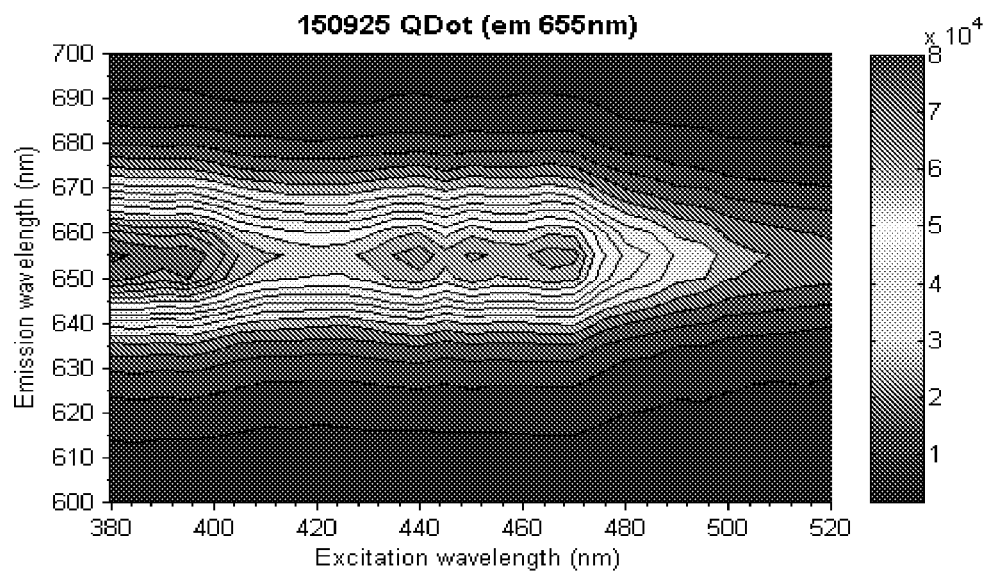

Fig. 5

| sample | vessel | tissue | buffer | concentration | ball bearings | | | relative copies DNA |
|---|---|---|---|---|---|---|---|---|
| | | | | | size | number | surface area | |
| 1 | eppendorf | 36mg | 1ml | 36mg/ml | 4mm | | 5,250mm$^2$ | 29 |
| 2 | bijoux | 20mg | 2ml | 10mg/ml | 4mm | | 10,500mm$^2$ | 1,373 |
| 3 | bijoux | 60mg | 5ml | 12mg/ml | 6mm | | 5,565mm$^2$ | 269 |
| 4 | bijoux | 60mg | 2ml | 30mg/ml | 4mm | | 10,500mm$^2$ | 4,783 |

Fig. 6

Fig. 7
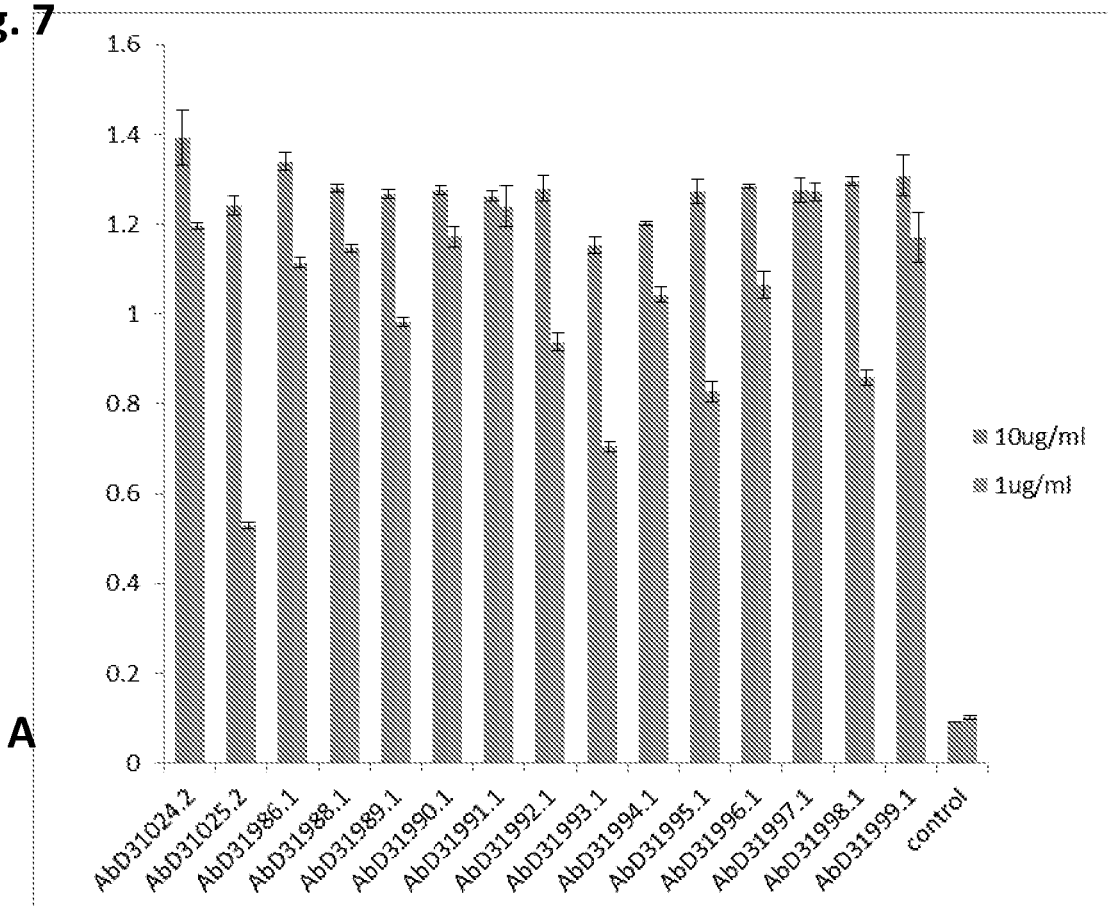
A
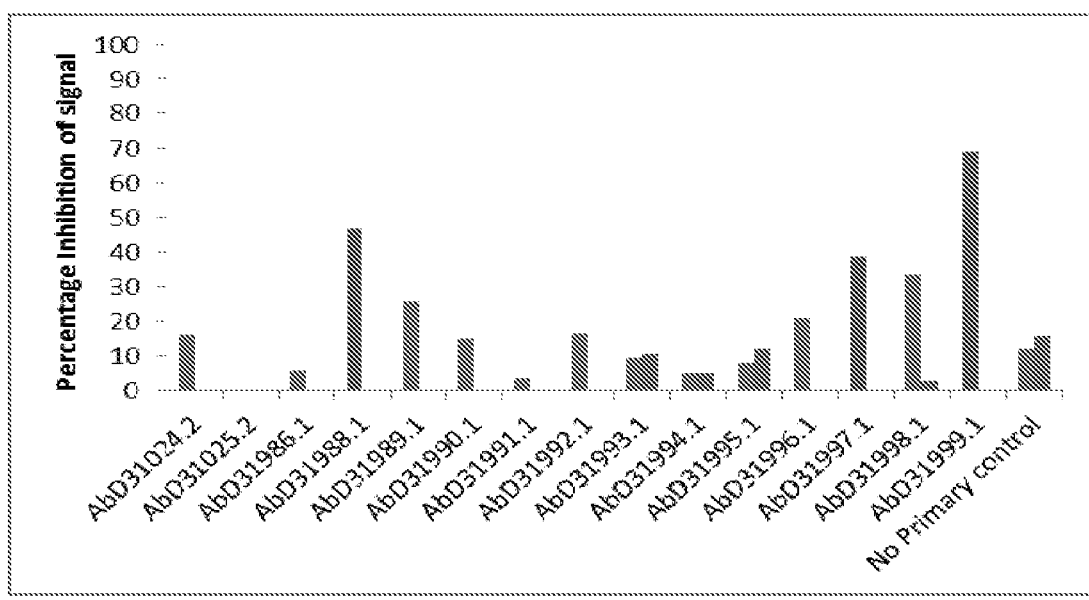
B

Fig. 12

Fig. 13
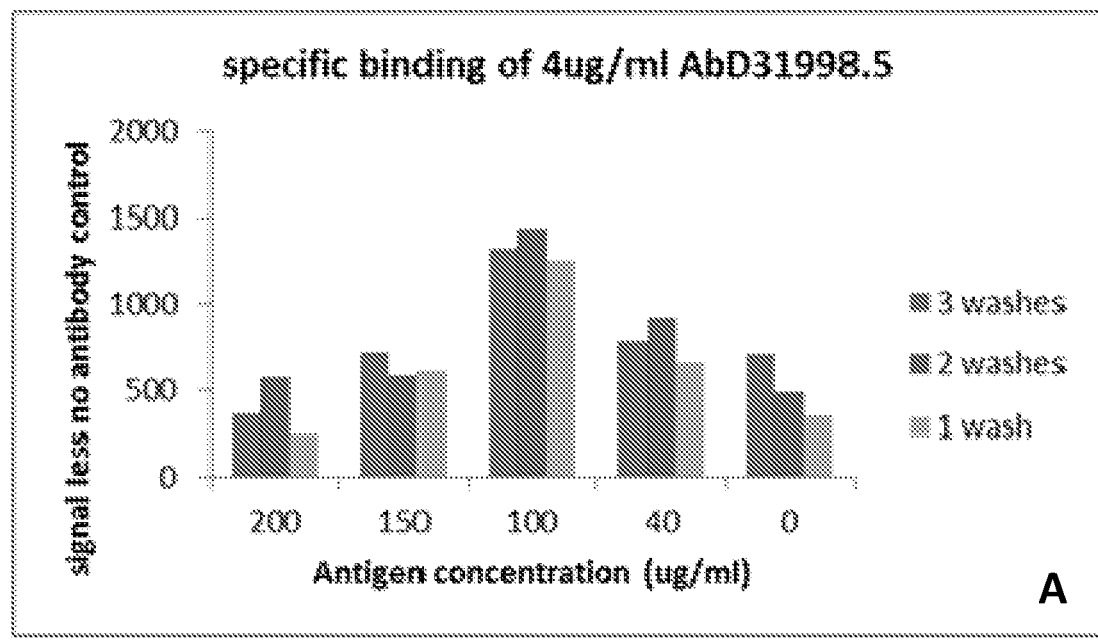
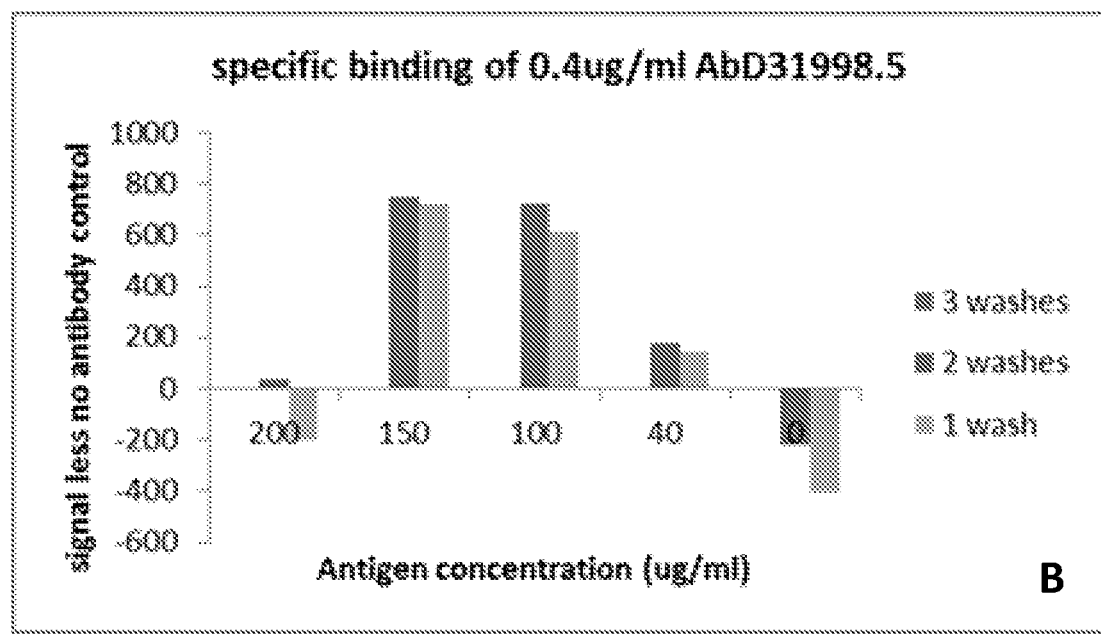

| Sample | Plant | Dilution | % Inhibition | Copies/cell | Sample | Plant | Dilution | % Inhibition | Copies/cell |
|---|---|---|---|---|---|---|---|---|---|
| 2 | G35 symptomatic A | 1/10 | 38.46153846 | 108.3 | 1 | G35 non symptomatic A | 1/10 | 6.054131054 | 2.9 |
|  |  | 1/100 | 36.32478632 |  |  |  | 1/100 | 30.84045584 |  |
|  |  | 1/1000 | 37.67806268 |  |  |  | 1/1000 | 19.08831909 |  |
| 4 | G35 symptomatic B | 1/10 | 56.48148148 | 90.1 | 3 | G35 non symptomatic B | 1/10 | 58.04843305 | 0.4 |
|  |  | 1/100 | 28.84615385 |  |  |  | 1/100 | 29.91452991 |  |
|  |  | 1/1000 | 12.96296296 |  |  |  | 1/1000 | 22.43589744 |  |
| 5 | G35 symptomatic C | 1/10 | 68.51851852 | 12.4 | 9 | G35 non symptomatic C | 1/10 | 33.02752294 | 0.5 |
|  |  | 1/100 | 30.98290598 |  |  |  | 1/100 | 17.66055046 |  |
|  |  | 1/1000 | 27.35042735 |  |  |  | 1/1000 | 19.49541284 |  |
| 6 | G35 symptomatic D | 1/10 | 66.66666667 | 45.8 | 10 | G35 non symptomatic D | 1/10 | 45.18348624 | 0.4 |
|  |  | 1/100 | 48.86039886 |  |  |  | 1/100 | 34.40366972 |  |
|  |  | 1/1000 | 30.84045584 |  |  |  | 1/1000 | 25.4587156 |  |
| 7 | G46 symptomatic A | 1/10 | 58.48623853 | 67.8 | 8 | G46 non symptomatic A | 1/10 | 48.39449541 | 0.4 |
|  |  | 1/100 | 22.70642202 |  |  |  | 1/100 | 23.62385321 |  |
|  |  | 1/1000 | 18.34862385 |  |  |  | 1/1000 | 27.06422018 |  |
| 22 | G46 symptomatic B | 1/10 | 47.32142857 | 333.5 | 19 | G46 non symptomatic B | 1/10 | 27.88461538 | 0.2 |
|  |  | 1/100 | 28.77747253 |  |  |  | 1/100 | 25.20604396 |  |
|  |  | 1/1000 | 27.06043956 |  |  |  | 1/1000 | 22.25274725 |  |
| 23 | G46 symptomatic C | 1/10 | 62.01923077 | 100.2 | 21 | G46 non symptomatic D | 1/10 | 51.51098901 | 1.9 |
|  |  | 1/100 | 34.06593407 |  |  |  | 1/100 | 21.84065934 |  |
|  |  | 1/1000 | 22.32142857 |  |  |  | 1/1000 | 6.799450549 |  |
| 24 | G46 symptomatic D | 1/10 | 60.50824176 | 298.8 | 29 | G46 non symptomatic E | 1/10 | 40.08528785 | 0.9 |
|  |  | 1/100 | 36.67582418 |  |  |  | 1/100 | 20.68230277 |  |
|  |  | 1/1000 | 23.48901099 |  |  |  | 1/1000 | 14.4989339 |  |
| 25 | G6 symptomatic A | 1/10 | 65.67164179 | 7.9 | 30 | G6 non symptomatic A | 1/10 | 31.87633262 | 0.2 |
|  |  | 1/100 | 28.9978678 |  |  |  | 1/100 | 16.95095949 |  |
|  |  | 1/1000 | 16.09808102 |  |  |  | 1/1000 | 15.99147122 |  |
| 26 | G6 symptomatic B | 1/10 | 68.86993603 | 6.4 | 31 | G6 non symptomatic B | 1/10 | 6.268556716 | 0.1 |
|  |  | 1/100 | 31.66311301 |  |  |  | 1/100 | 6.417910448 |  |
|  |  | 1/1000 | 12.79317697 |  |  |  | 1/1000 | 8.805970149 |  |
| 27 | G6 symptomatic C | 1/10 | 63.64605544 | 254.6 | 32 | G6 non symptomatic C | 1/10 | 24.17910448 | 0.4 |
|  |  | 1/100 | 23.34754797 |  |  |  | 1/100 | 8.955223881 |  |
|  |  | 1/1000 | 4.47761194 |  |  |  | 1/1000 | 6.119402985 |  |
| 28 | G6 symptomatic D | 1/10 | 47.65458422 | 16.6 | 20 | G6 non symptomatic C | 1/10 | 32.55494505 | 1 |
|  |  | 1/100 | 18.86993603 |  |  |  | 1/100 | 29.46428571 |  |
|  |  | 1/1000 | 16.09808102 |  |  |  | 1/1000 | 31.93681319 |  |

TOOLS FOR DETECTING COCOA SWOLLEN SHOOT VIRUS COAT PROTEIN ANTIGEN

CROSS REFERENCE TO RELATED APPLICATIONS

This application is a U.S. National Phase Patent Application of PCT/GB2019/053056, filed internationally Oct. 29, 2019, which claims priority to and the benefit of Great Britain Patent Application No. 1817721.2, filed Oct. 30, 2018 and Great Britain Patent Application No. 1908311.2, filed Jun. 11, 2019.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 14418-20037.00SEQLIST.TXT, date recorded: Apr. 23, 2021, size: 44 KB).

FIELD OF INVENTION

The present invention relates to detecting viral infections in plants, especially Cacao swollen-shoot virus (CSSV) infections. Recombinant viral coat protein antigens and binding reagents that specifically bind to thereto are provided together with a sensor incorporating the recombinant antigens. A competitive ELISA for detecting viral infections in plants is also provided.

BACKGROUND TO THE INVENTION

Cacao swollen-shoot virus (CSSV) is a plant pathogen Badnavirus that infects *Theobroma cacao* trees (cacao trees), decreasing cacao yields and ultimately killing the trees within 3-4 years from infection. Surveys show that in Ghana, for example, around 17% of the cacao growing region is infected. Ghana has had a nationwide cutting out and rehabilitation programme which has resulted in at least 34 million trees being cut down since 2006. Despite many years of these procedures, CSSV infection has spread and is increasing. CSSV therefore presents a major problem for commercial cacao production.

CSSV infection occurs only in plant tissue and is not present in seeds. Current control measures include visual inspection by local government agencies of trees and removal of those infected and nearby trees. For visible symptoms to appear, trees may have been infected for many months prior to identification, enabling the possibility of significant disease transmission. Furthermore, CSSV infection is spread by wind carriage of up to fourteen species of the mealybug (Pseudococcidae) vector, leading to a significant range for disease transmission, and control measures for the vector have so far proved ineffective. In addition, although CSSV symptoms once manifested are usually distinctive, it can be difficult to distinguish the disease from other stresses such as nutrient deficiencies and effects of drought.

The current technology that is used to detect CSSV is based on the detection of viral DNA using a polymerase chain reaction (PCR) (Dzahini-Obiatey, 2010 and Oro et al., 2012). This can only be performed in a laboratory environment and by trained staff. There are PCR systems being developed for other applications that could be deployed in the field but the assays are very expensive and require skilled personnel.

There are a number of simple field testing devices for detection of plant virus infection of other crops, these are based on lateral flow technologies (e.g. Pocket Diagnostic, Abingdon Health Ltd UK). Despite the growing threat to cacao plants from CSSV and the increasing demand for cocoa beans to date, however, none have been developed for CSSV. Despite their ease of use, lateral flow devices typically lack sensitivity and interpretation is often subjective.

The need therefore remains for an assay system that is inexpensive and can be used by unskilled personnel on-site to carry out surveillance procedures and, unlike with standard lateral flow devices, is sufficiently sensitive and specific. Such a system would enable cocoa seedlings to be tested prior to planting and mature cocoa plants to be monitored in the field for CSSV infection. This will help to identify the rate and spread of CSSV disease to be mapped and will enable protection methods to be deployed in areas of low or no infection. This is of critical importance to cocoa growers and multinational users. The present invention aims to provide such a system.

SUMMARY OF THE INVENTION

Accordingly, in a first aspect, the present invention provides a method for detecting Cocoa Swollen Shoot Virus (CSSV) using a porous membrane based sensor, the sensor comprising at least one recombinant CSSV coat protein antigen having at least 80% sequence identity to the amino acid sequence of SEQ ID NO: 2 or 4, the method comprising the steps of: (i) contacting cocoa plant material with a labelled binding reagent that specifically binds to the recombinant coat protein antigen to produce a mixture comprising the plant material and binding reagent; and (ii) contacting the mixture with the membrane based sensor.

The recombinant CSSV coat protein antigens have been developed by the present inventors to provide a universal CSSV coat protein antigen that can be used to develop binding reagents and in assays. The recombinant coat protein antigens have been prepared based on the analysis of Open Reading Frame 3 (ORF3) of multiple CSSV genomes and using highly conserved regions of CSSV capsid protein. The recombinant coat protein antigens can be used to generate binding reagents capable of accurately detecting multiple CSSV variants, whilst limiting or avoiding cross reactions with other viruses such as other badnaviruses.

In a second aspect the present invention provides an assay for detecting a viral infection in a plant, the assay comprising the steps of:

contacting plant material with a labelled recombinant binding reagent that specifically binds to a viral coat protein antigen to produce a mixture comprising the plant material and labelled binding reagent; and contacting the mixture with viral coat protein antigen which is immobilised in or on a surface;

removing labelled recombinant binding reagent that is not bound to the immobilised viral coat protein antigen; and detecting the presence of the remaining labelled recombinant binding reagent to determine the presence or absence of the viral infection, wherein the amount of labelled recombinant binding reagent detected is inversely correlated with the number of viral particles present in the plant material.

In a third aspect the present invention provides an isolated binding reagent that specifically binds to a recombinant Cocoa Swollen Shoot Virus (CSSV) coat protein antigen having at least 80% sequence identity to the amino acid sequence of SEQ ID NO: 2 or 4 and/or at least 80% sequence identity to the nucleotide sequence of SEQ ID NO: 1 or 3.

In a fourth aspect the present invention provides a porous membrane based sensor for detecting CSSV comprising a recombinant CSSV coat protein antigen. The sensor can be used in the field to detect CSSV in asymptomatic plants and can reduce or avoid the need for expensive laboratory testing. Additionally, the sensor of the present invention allows the testing to be carried out by unskilled personnel with the consequence that testing can made more widely accessible to cocoa growers.

DESCRIPTION

The isolated binding reagent of the present invention specifically binds to a recombinant CSSV coat protein antigen having at least 80% sequence identity to the amino acid sequence of SEQ ID NO: 2 or 4 and/or at least 80% sequence identity to the nucleotide sequence of SEQ ID NO: 1 or 3.

Whilst the genome sequences of several strains of CSSV have been published, these sequences are not fully annotated. Consequently, whilst the skilled person might know approximately where a protein would be located in the genome they would not know exactly where the protein starts and ends within that genome sequence. The present inventors reviewed five published CSSV genome sequences and aligned them with over 20 other badnavirus sequences to identify conserved regions likely to form part of the coat protein antigen. The C-terminal region of the coat protein was identified based on a conserved zinc knuckle domain in ORF 3 and, from previous SDS page analysis of coat proteins, a sequence length of up to 345 amino acids was identified. The inventors then searched the aligned sequences within the boundary of 345 amino acids and identified a conserved site across the five published CSSV reference strains, which forms the N-terminus and generates a 334 amino acid sequence (SEQ ID NO:2). The corresponding DNA sequence (1002 bp; SEQ ID NO:1) was identified on a highly virulent New Juaben strain and the recombinant protein was produced by inserting the sequence into a vector and expressing the vector in *E. coli*. This produced the recombinant coat protein antigen of SEQ ID NO:2. Subsequently, 30 additional CSSV sequences were published (Muller et al., 2017; Chingandu et al., 2017) and the above approach was repeated to provide the recombinant coat protein antigen of SEQ ID NO:4 and the corresponding nucleotide sequence of SEQ ID NO:3.

The recombinant coat protein antigens described herein therefore do not include the full coat protein sequence and do not correspond to any one naturally occurring CSSV coat protein antigen. The recombinant coat protein antigens can therefore be used to generate binding reagents able to detect multiple strains of CSSV, which contrasts with known anti-CSSV antibodies, which typically only detect one strain. Additionally, because the binding reagents are generated using recombinant coat protein antigens rather than using plant material, high levels of background activity can be reduced or avoided. The binding reagents generated from the recombinant coat protein antigens can therefore provide more sensitive tests because they can correctly identify the presence of lower concentrations of CSSV in a sample.

In embodiments of the invention the isolated binding reagent may bind to a recombinant CSSV coat protein antigen having at least 85%, or at least 90%, or at least 95% sequence identity with one or more of SEQ ID NOs:1-4. The recombinant CSSV coat protein antigen may comprise a sequence having at least 98% or 99% or 100% sequence identity with one or more of SEQ ID NOs:1-4. In embodiments of the invention the recombinant CSSV coat protein antigen may consist of a sequence having at least 85%, or at least 90%, or at least 95% sequence identity with one or more of SEQ ID NOs:1-4. The recombinant CSSV coat protein antigen may consist of a sequence having at least 98% or 99% or 100% sequence identity with one or more of SEQ ID NOs:1-4. In embodiments of the invention the recombinant CSSV coat protein antigen may consist of a sequence according to any one of SEQ ID NOs: 1-4. The recombinant CSSV coat protein antigens can be used to generate binding reagents that can detect multiple strains of CSSV, whilst avoiding false positives.

In the description above, the term "identity" is used to refer to the similarity of two sequences. For the purpose of this invention, it is defined here that in order to determine the percent identity of two sequences, the sequences are aligned for optimal comparison purposes (e.g., gaps can be introduced in the sequence of a first sequence for optimal alignment with a second amino or nucleic acid sequence). The nucleotide/amino acid residues at each position are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Generally, the two sequences are the same length. A sequence comparison is typically carried out over the entire length of the two sequences being compared.

The skilled person will be aware of the fact that several different computer programs are available to determine the identity between two sequences. For instance, a comparison of sequences and determination of percent identity between two sequences can be accomplished using a mathematical algorithm. For example, the percent identity between two nucleic acid sequences can be determined using the sequence alignment software Clone Manager 9 (Sci-Ed software www.scied.com) using global DNA alignment; parameters: both strands; scoring matrix: linear (mismatch 2, OpenGap 4, ExtGap 1).

Alternatively, the percent identity between two amino acid or nucleic acid sequences can be determined using the Needleman and Wunsch (1970) algorithm which has been incorporated into the GAP program in the Accelrys GCG software package www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. A further method to assess the percent identity between two amino acid or nucleic acid sequences can be to use the BLAST sequence comparison tool available on the National Center for Biotechnology Information (NCBI) website (www.blast.ncbi.nlm.nih.gov), for example using BLASTn for nucleotide sequences or BLASTp for amino acid sequences using the default parameters.

The binding reagent that specifically binds to the recombinant CSSV coat protein antigen is typically recombinant and may be an antibody, an aptamer, an affimer, or a DNA binding protein. Preferably the binding reagent is an antibody such as a monoclonal antibody or a polyclonal antibody. Most preferably the binding reagent is a recombinant monoclonal antibody, such as a recombinant F(ab)2 monoclonal antibody.

Suitable monoclonal antibodies may comprise the CDRs of SEQ ID NOs: 8-13 or SEQ ID NOs: 16-21 or SEQ ID NOs: 24-29. For example, the monoclonal antibody may comprise a light chain variable region sequence selected from SEQ ID NOs: 7, 16 or 25 and a heavy chain variable region sequence selected from SEQ ID NOs: 6, 15 or 24. In particular, the monoclonal antibody may comprise the light chain variable region of SEQ ID NO: 7 and the heavy chain variable region of SEQ ID NO: 6; or the light chain variable region of SEQ ID NO: 16 and the heavy chain variable region of SEQ ID NO: 15; or the light chain variable region of SEQ ID NO: 25 and the heavy chain variable region of SEQ ID NO: 24. The monoclonal antibody may comprise or consist of an amino acid sequence of having at least 80% sequence identity to SEQ ID NOs: 5, 14 or 23.

Monoclonal antibodies as described herein have been shown to detect multiple strains of CSSV, including New Juaben, Kpeve and Nsaba.

The binding reagent may be conjugated to a label, such as a fluorescent label, to provide a labelled binding reagent. Fluorescent labels that might be used include eosin, fluorescein, cyanine dyes, nanoparticles with fluorescent characteristics (e.g. EUIII and up converting nanoparticles (UNCPs)) and quantum dots.

Many fluorescent labels can have poor signal to noise ratios and decompose on prolonged re-stimulation because of photo-bleaching. Additional problems can be encountered due to quenching of the signal by the sample and other components in the solution, and optical absorption at the measurement wavelengths. Quantum dots provide photostability, broad adsorption spectra and intense narrow emission spectra. Accordingly, whilst other labels can be used, quantum dots are a preferred label.

Suitable labels may have emission wavelengths in the infrared or near-infrared ranges. For example, the label may have emission wavelengths of about 500 nm to about 600 nm, and/or about 700 nm to about 1000 nm, preferably about 700 nm to about 900 nm, more preferably about 800 nm. The emission wavelength of the label preferably avoids peak chlorophyll emission and adsorption (as shown in Fernandez-Jaramillo et al, 2012).

The present invention additionally provides a porous membrane based sensor for detecting CSSV comprising a recombinant CSSV coat protein antigen (as described above). The sensor can be used in the field to detect CSSV in asymptomatic plants and is suitable for use by unskilled personnel. The sensor may be formed from layers of membrane, such as nitrocellulose, polycarbonate or other high protein binding porous membrane, which act as a solid phase for immobilisation of capture reagents and allow the reagents and sample to move through the membranes by capillary flow.

Preferably the sensor comprises a superficial sieve layer having a pore size of at least 1 μm. The sieve layer acts to remove plant debris from the sample. The sieve layer may have pore size of about 10 μm to about 1000 μm, preferably about 1 μm to about 800 μm, more preferably about 20 μm to about 30 μm. In embodiments of the invention the sieve layer may have a pore size of about 25 μm. The sieve layer may be formed from a material such as rayon polyester.

Preferably the sensor additionally comprises a capture layer in the form of a porous membrane layer in which the at least one recombinant CSSV coat protein antigen is immobilised. The membrane may have pore size of about 0.05 μm to about 20 μm, preferably about 0.1 μm to about 1 μm. In embodiments of the invention the membrane layer may have a pore size of about 0.8 μm. Target present in the sample competes with the immobilised antigen for binding to a labelled binding reagent (as described above). The capture layer may be formed from materials such as nitrocellulose.

Preferably the sensor additionally comprises a sink layer in the form of an absorbent layer adjacent the capture layer. The sink layer acts to draw liquid through the layers of the sensor. The sink layer may be formed from materials such as cellulose, cotton linter fibres, wood pulp, and sodium polyacrylate super-absorbent polymers or mixtures thereof.

Preferably the sensor additionally comprises a blocking layer in the form of a porous non-reflective layer between the capture layer and the sink layer. This layer acts to prevent light exciting any unbound reporter in the sink layer, thereby reducing nonspecific background signal.

Plant material can be mixed with a labelled binding reagent prior to being contacted with the sensor. The sieve layer removes plant debris and any free/unbound labelled binding reagent binds to the immobilised antigen in the capture layer. Labelled binding reagent bound to antigen (CSSV) in the sample is not immobilised in the capture layer and is drawn into the sink layer. The blocking layer prevents labelled binding reagent in the sink layer from being detected. The signal is detected from labelled binding reagent bound to the immobilised antigen in the capture layer and the amount of the labelled binding reagent present will be inversely correlated with the amount of CSSV present in the plant material.

The present invention additionally provides a method for detecting Cocoa Swollen Shoot Virus (CSSV) using a porous membrane based sensor as described above, the method comprising the steps of:
  (i) contacting cocoa plant material with a labelled binding reagent as described herein to produce a mixture comprising the plant material and binding reagent; and
  (ii) contacting the mixture with the membrane based sensor.

The cocoa plant material may be any plant material and is preferably leaf or stem material. The use of cocoa plant stem material may provide particular advantages as the virus can be extracted by soaking the stems (i.e. no maceration required) and because stems do not contain chlorophyll, so they don't have the problems associated with chlorophyll autofluoresence that can be encountered when using leaf material.

The present invention additionally provides an assay for detecting a viral infection in a plant, the assay comprising the steps of:
  contacting plant material with a labelled recombinant binding reagent that specifically binds to a viral coat protein antigen to produce a mixture comprising the plant material and binding reagent;
  contacting the mixture with viral coat protein antigen which is immobilised in or on a surface;
  removing labelled recombinant binding reagent that is not bound to the immobilised viral coat protein antigen; and
  detecting the presence of the remaining labelled recombinant binding reagent to determine the presence or absence of the viral infection, wherein the amount of labelled recombinant binding reagent detected is inversely correlated with the number of viral particles present in the plant material.

The viral coat protein antigen may be a recombinant antigen. The viral coat protein antigen may be a recombinant CCSV coat protein antigen as described above.

The labelled recombinant binding reagent may be an antibody. For example, the recombinant binding reagent may be a binding reagent according to the first aspect of the invention.

The virus may be a Badnavirus, the Badnavirus may be CSSV.

The label may be a fluorescent label as described above. For example, the label may be a quantum dot having an excitation wavelength of at least 600 nm.

BRIEF DESCRIPTION OF THE DRAWINGS

The invention will now be described in detail, by way of example only, with reference to the figures.

FIG. 2 shows fluorescence emission excitation matrices (EEMs) for 605 and 705 nm Quantum Dots (QDs).

FIG. 5 shows results of the assessment of the efficiency of release of virus from CSSV infected *Theobroma cacao* leaf tissue by ball bearings.

Figure 6:
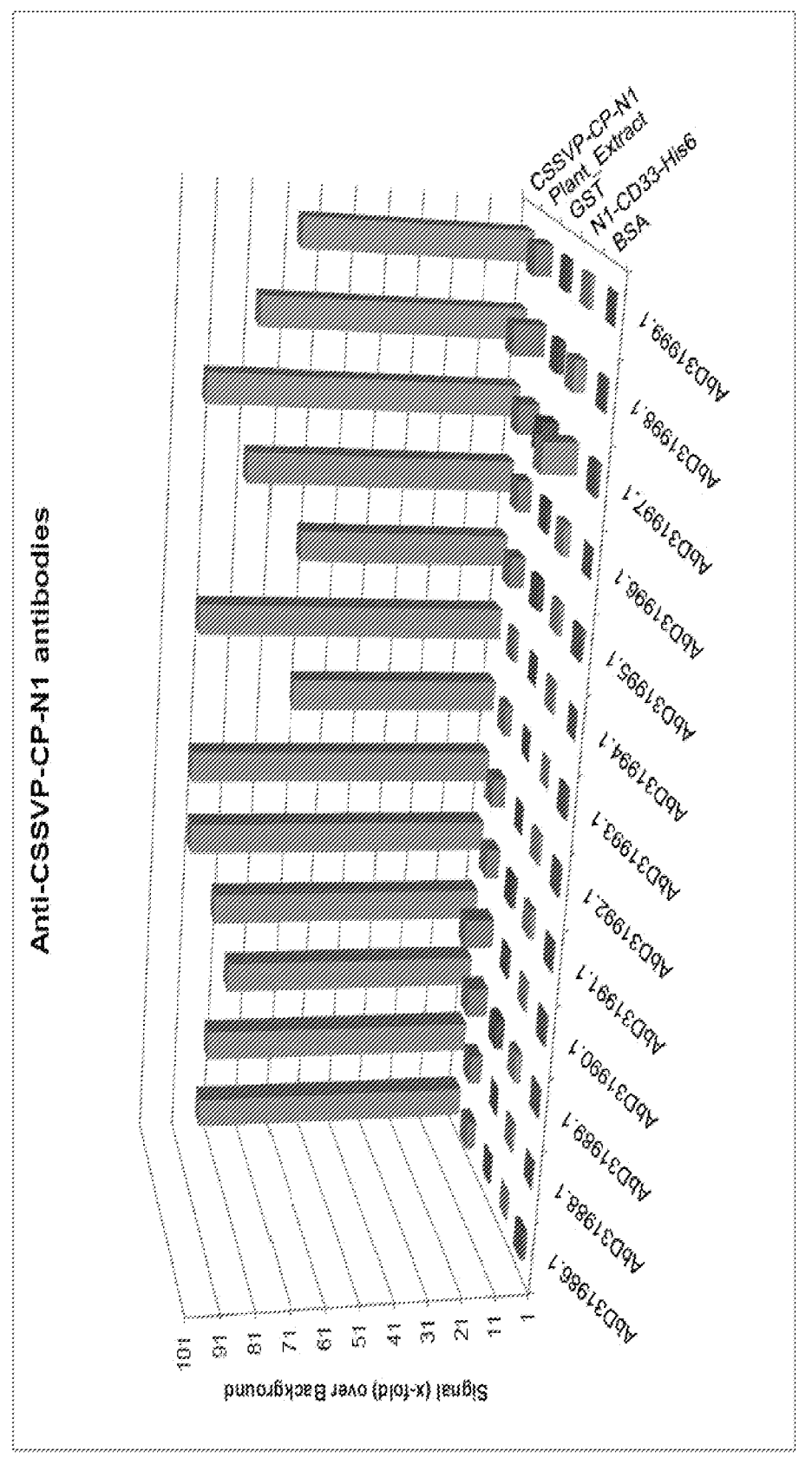

FIG. 6 shows a bar chart illustrating the selectivity of candidate recombinant antibodies. Anti-CSSV-CP-01 antibodies that bind to CSSV-CP-01 but not 1/100 dilution of CSSV negative *Theobroma cacao* plant extract, BSA, N1-CD33-HIS tag nor unrelated protein with N1-CD33-HIS6 tag. (Data provided by manufacturer.)

FIG. 7 shows A: results of a direct ELISA assay to confirm binding of fifteen candidate anti-CSSV recombinant antibodies to recombinant CSSV coat protein antigen (CSSV-CP-01), n=3; and B: Competitive ELISA results showing percentage inhibition produced by CSSV positive and negative plant extract, n=2, of the interaction between fifteen anti-CSSV recombinant antibodies to CSSV-CP-01 antigen.

Figure 12:
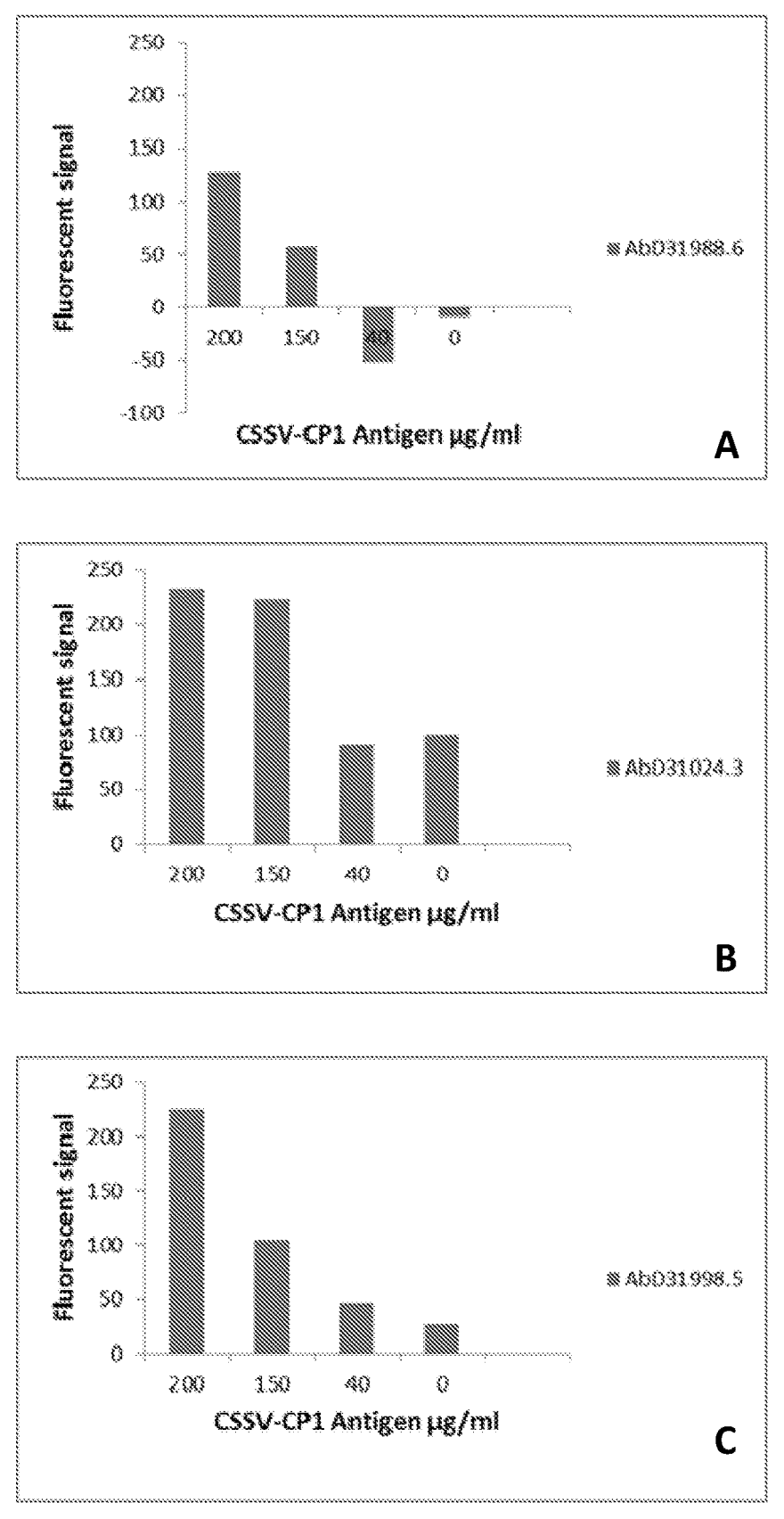

FIG. 12 shows the binding of different recombinant monoclonal antibodies to a range of concentrations of CSSV-CP-01 antigen using a CSSV biosensor as described herein.

FIG. 13 shows the binding of two concentrations of biotinylated recombinant monoclonal antibody AbD 31998.5 binding to a range of concentrations of CSSV-CP-01 antigen using a CSSV biosensor as described herein.

Figures 14, 15:
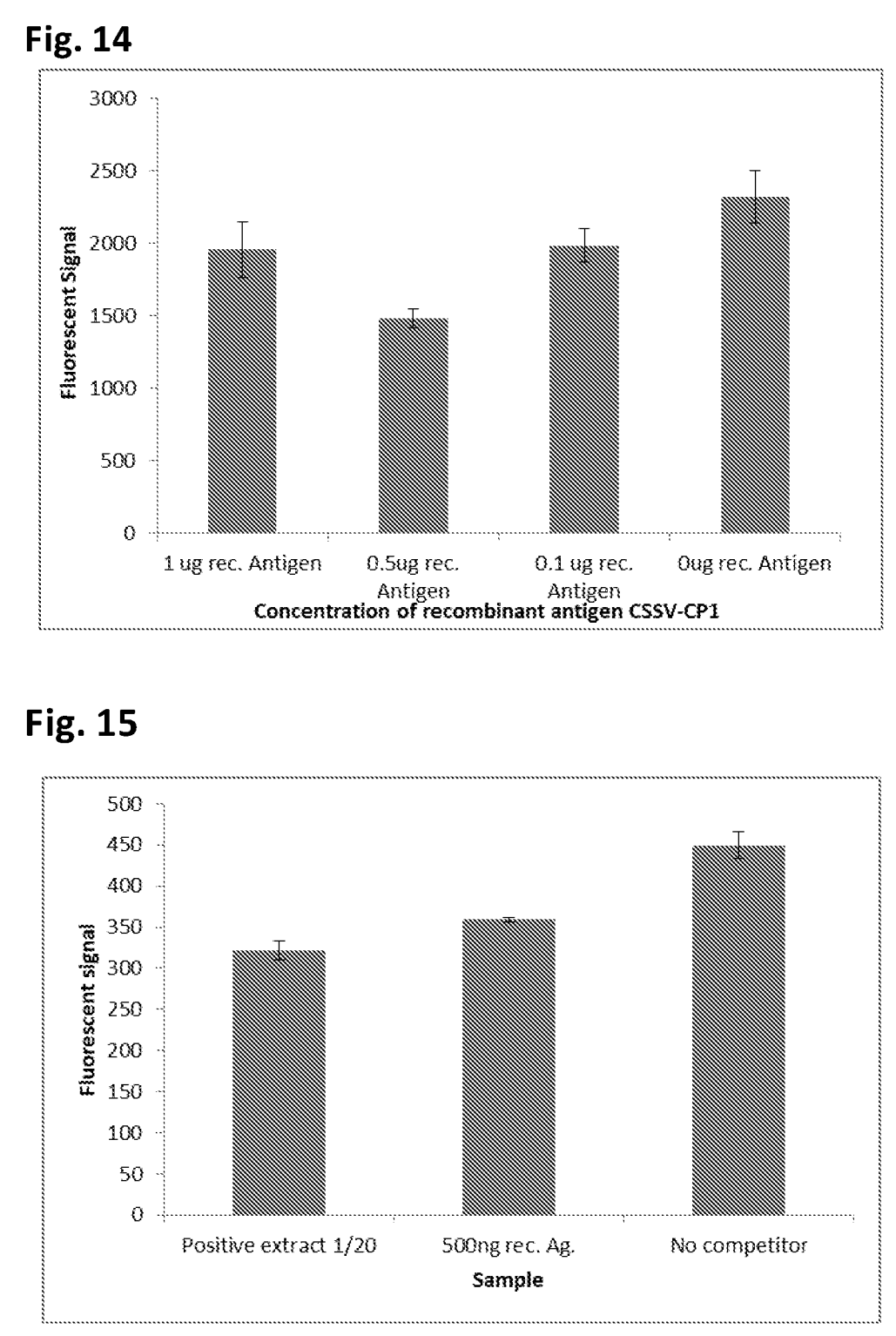

FIG. 14 shows results of competition of the binding of biotinylated recombinant monoclonal antibody AbD 31998.5 to CSSV-CP-01 antigen by a range of concentrations of free CSSV-CP-01 antigen (n=3).

FIG. 15 shows results from a biosensor demonstrating competition by CSSV positive plant extract (n=3).

FIG. 16 shows a conceptual diagram of the CSSV biosensor detection system for use in the field.

FIG. 17 shows fluorescence obtained with controls and free CSSV-CP-01 measured in the biosensor during field trials.

FIG. 18 shows a comparison of the mean number of CSSV copies/cell present in CSSV infected symptomatic leaves, CSSV infected non-symptomatic leaves and uninfected (negative) leaves.

FIGS. 19A and 19B represent summary data of ELISA assays performed. A: graph showing dose response of CSSV recombinant protein. B: Graph showing mean and SE of multiple leaves taken from the same plant.

FIG. 21 shows CSSV competitive ELISA and Taqman qPCR results for individual infected CSSV plant extracts. All samples with >45% inhibition in the CSSV competition ELISA had 0.4 CSSV DNA copies/cell. These samples are marked as positive for CSSV.

FIG. 22 shows a comparison of three anti-CSSV recombinant antibodies in the competitive CSSV ELISA at 1.25 µg/ml of CSSV antigen 1 (CSSV-CP-01).

FIG. 23 shows the interaction of recombinant monoclonal antibodies with CSSV-CP-01 and CSSV-CP-02.

EXAMPLES

Work conducted at The University of the West of England (UWE), Bristol established a strategy to develop a rapid hand held in field biosensor to detect Cocoa Swollen Shoot Virus (CSSV) infection of *Theobroma cocoa*.

Evaluation of Florescent Reporter

Figure 1:
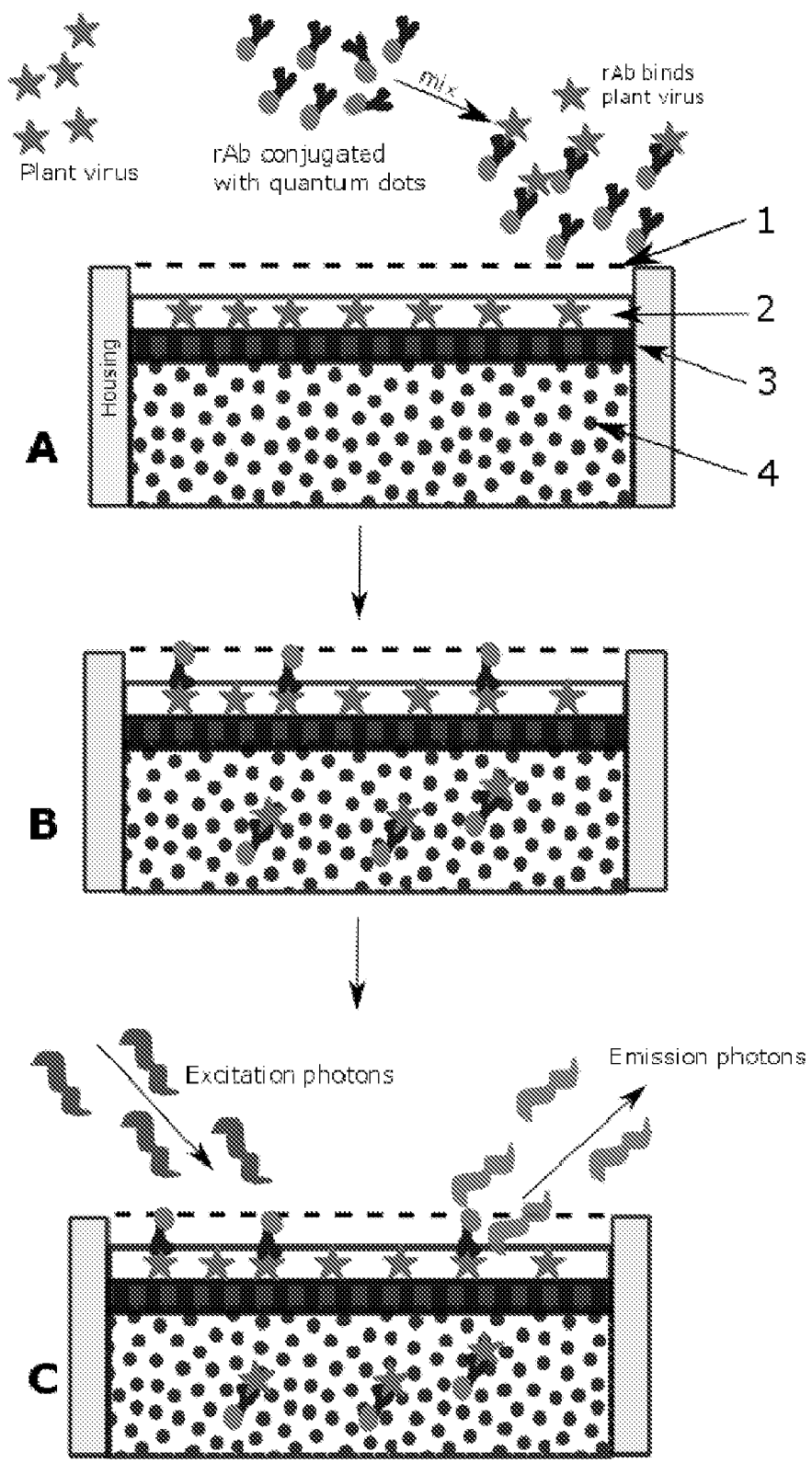
FIG. 1 shows a schematic of an embodiment of the porous membrane based sensor. A shows an arrangement of porous layers including: 1. a sieve layer formed of a large pored membrane used to exclude plant debris; 2. a capture layer formed of a porous membrane containing immobilised antigen (e.g. a recombinant viral coat protein); 3. a dark layer formed of a porous layer; and 4. a sink layer in the form of an absorbent material to pull liquid through the superficial porous membranes. B shows movement of the sample through the membrane by capillary action. Free recombinant antibody/reporter (e.g. quantum dots) binds to the recombinant viral coat protein immobilised in the capture layer (2). Antibody/reporter bound to plant virus in the sample passes through the membrane (3) and is taken up by the sink (4). C The sensor is exposed to a light source which causes the reporter to exhibit a strong fluorescence at a defined wavelength depending on the reporter used, e.g. depending on the diameter of quantum dots. Dark layer 3 prevents light exciting unbound fluorescent reporter in sink layer 4, thereby reducing nonspecific background signal.
Figure 3:
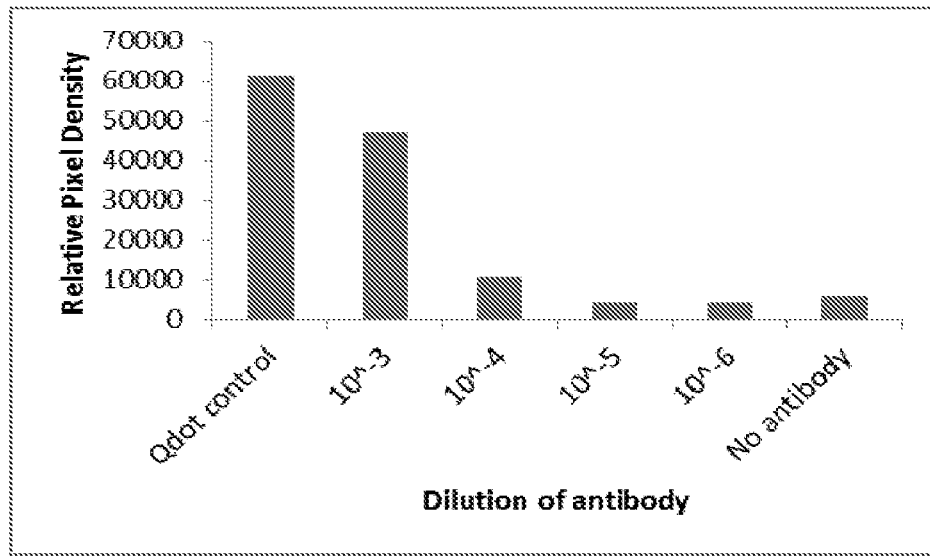
FIG. 3 shows pixel density of streptavidin tagged QDs 605 nm captured on nitrocellulose membrane at a range of concentrations of biotinylated goat anti-rabbit antibody. Measurements taken with an AlphaImager and analysed using ImageJ software.

Quantum dots (QDs) were evaluated as a fluorescent reporter and were shown to fluoresce at specific wavelengths dependant on the size of the quantum dots (FIG. 2). Pilot work showed the proof of concept to use streptavidin tagged quantum dots binding biotin conjugated antibody captured on a rapid flow through paper based cassette (FIG. 3). Other membrane types evaluated include PVDF, Polycarbonate and mixed Cellulose Ester (Data not shown).

Three ESELog ESML10-MB-3018 confocal fluorescence detectors were commissioned and produced with two excitation wavelengths:

E1—365 nm, E2—660 nm and two emission filters D1—625 nm, D2—720 nm.

Figure 4A:
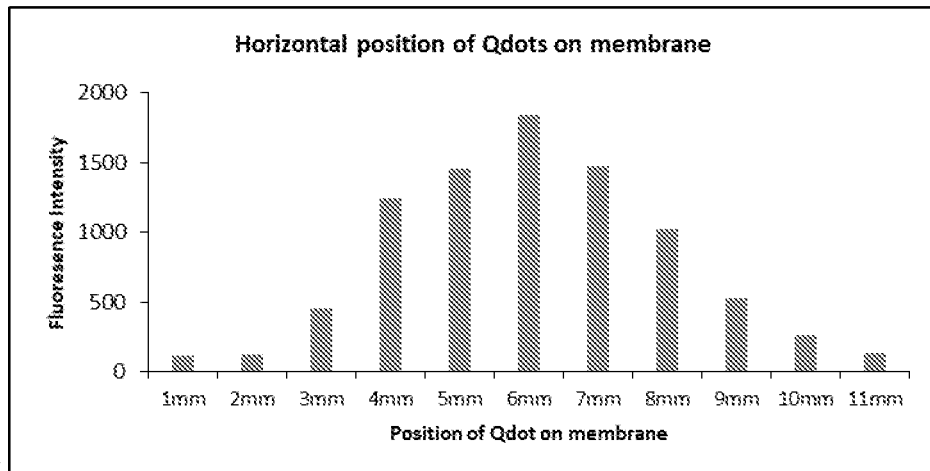
FIG. 4 shows bar graphs illustrating optimal horizontal (A) and vertical (B) positioning of QDs on the membrane for detection of fluorescence by ESElog Fluorimeters.
Figure 4B:
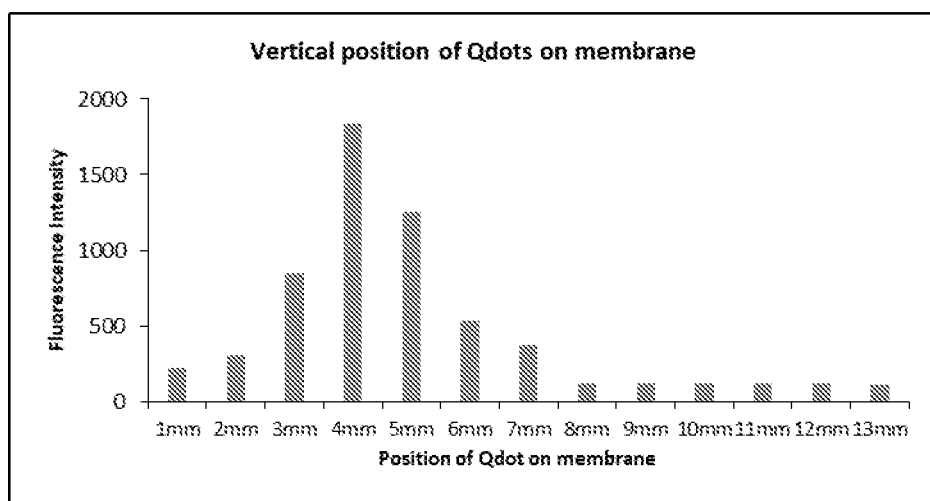
Figure 8:
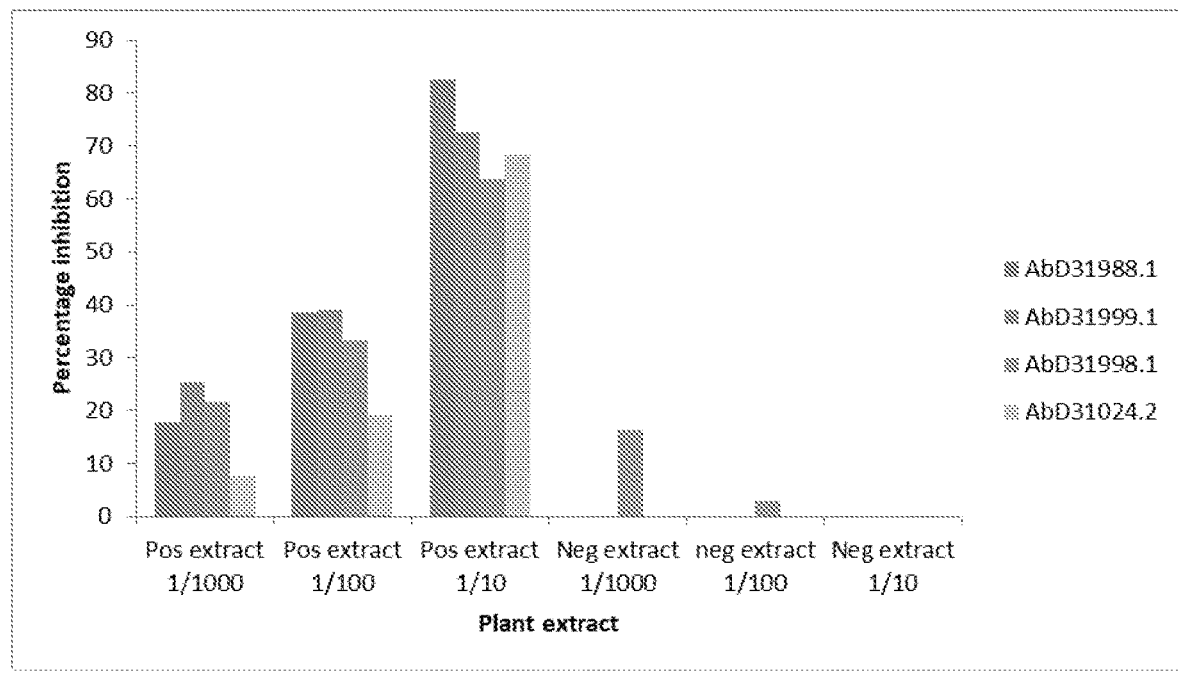
FIG. 8 shows competitive ELISA results for selected recombinant monoclonal antibodies with CSSV positive and negative plant extracts (n=2). The results shown are the average of two experiments with n=3 for each experiment, different leaves were tested in each experiment for selected recombinant antibodies at a range of dilutions of CSSV positive and negative plant extract.
Figure 9:
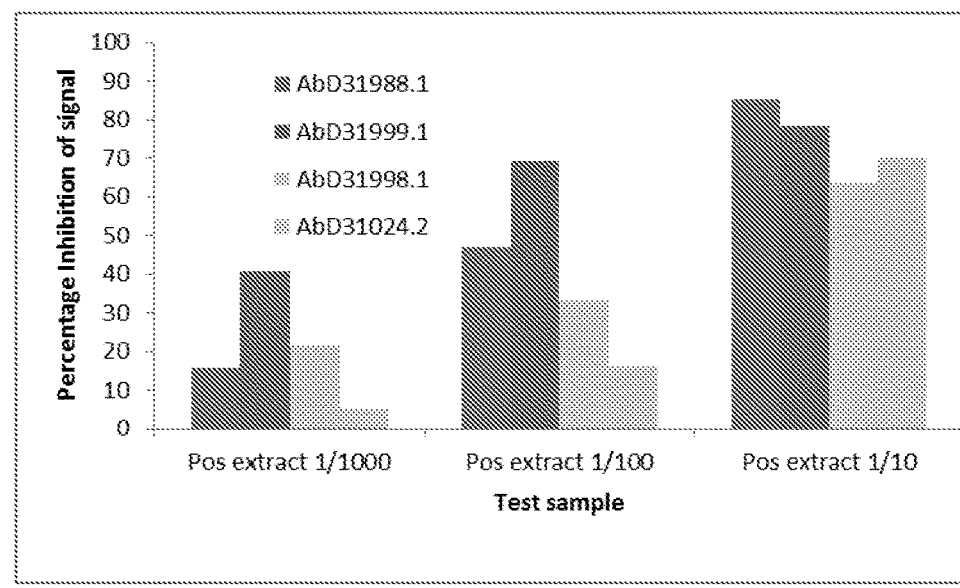
FIG. 9 shows the results of a competitive ELISA results with a qPCR confirmed CSSV infected plant samples and the effect of binding of recombinant antigen CSSV-CP-01 and recombinant monoclonal antibodies Ab31988.1, Ab31999.1, AbD31998 and AbD31024.1.
Figure 10:
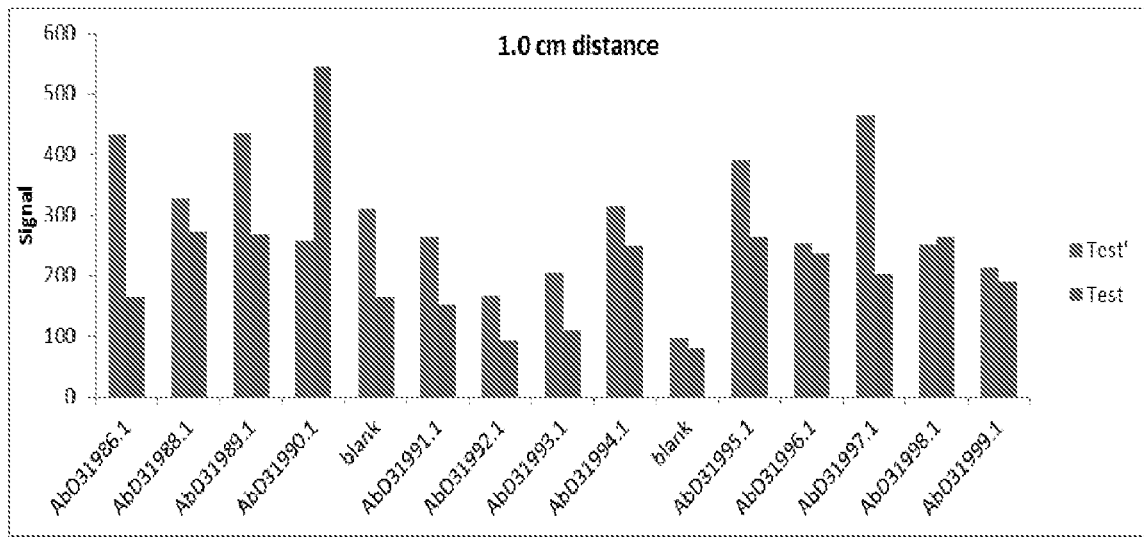
FIG. 10 shows detection of binding of recombinant monoclonal antibodies to antigen CSSV-CP-01, using biotinylated recombinant monoclonal antibody AbD31024.3 and a CSSV biosensor as described herein n=2.
Figure 11:
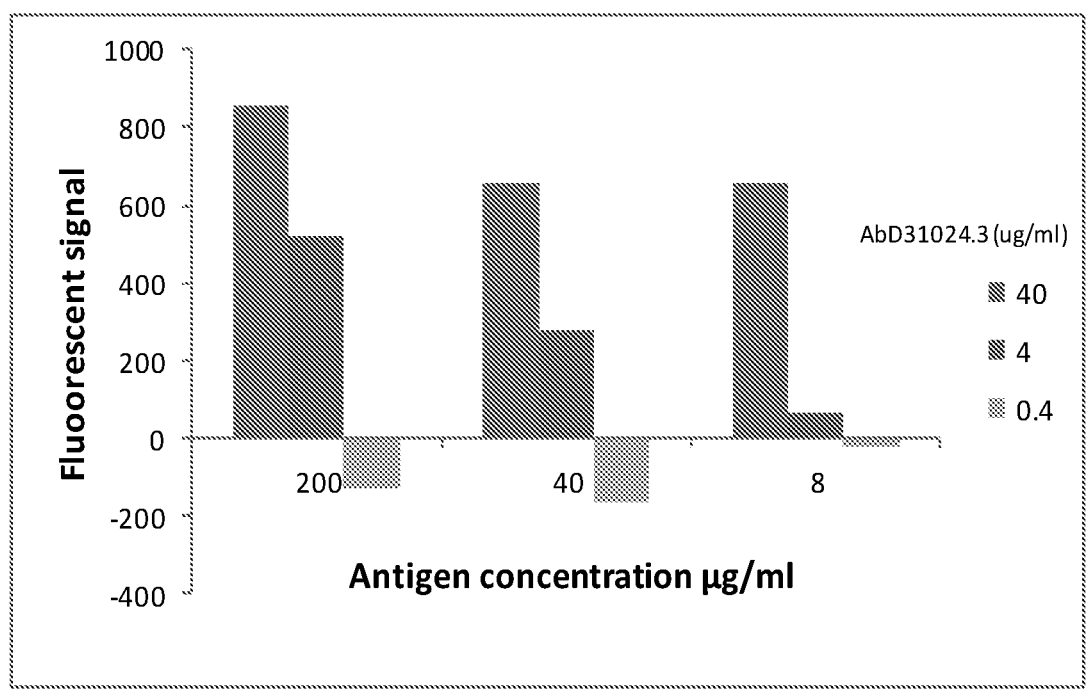
FIG. 11 shows binding of a range of concentrations of biotinylated CSSV antibody AbD31024.3 to a range of concentrations of recombinant antigen CSSV-CP-01 using a CSSV biosensor as described herein.

On evaluation it was found that the positioning of the quantum dots on the membrane gave maximum readings when positioned off centre (see FIGS. 4A and B).

Sequence Analysis of Published CSSV Sequences to Establish the ORF3 Region of CSSV Associated with the Viral Coat Protein.

Antibodies raised to virus purified from plant leaves have shown high background values in immunoassays. A strategy was developed to determine the CSSV coat protein sequence by alignment with other similar viral sequences and to produce a recombinant CSSV coat protein antigen (CSSV-CP-01). This would then be used to generate recombinant binding reagents e.g. Aptamers, Monoclonal Antibodies or Affimers, by phage display; this would therefore limit background interference as no plant material was used in the selection process. Research was performed into the costs, requirements and risk of the selection process, which led to a final choice of generation of recombinant Monoclonal Antibodies by phage display.

Tables 1 & 2 show reagents and equipment produced.

TABLE 1

Reagents produced.

| Reagents produced | Details |
|---|---|
| Recombinant CSSV coat protein antigen/ CSSV-CP-01. Two batches were synthesised, purified and used in the experiments shown CSSV-CP-01a and CSSV-CP-01b | Based on x5 published sequences |
| Recombinant CSSV coat protein antigen/ CSSV-CP-02. | Based on sequences from Muller et al., 2018 and Chingandu et al., 2017 |
| Recombinant monoclonal antibodies | Produced by phage display |
| Polyclonal antibody produced in rabbits | Inoculum CSSV-CP-01a |

TABLE 2

Equipment produced

| Equipment produced | Details | Additional information |
|---|---|---|
| ESELog fluorimeters | X3 produced | Narrow beam Range of emissions detected |
| 3D printed holder for fluorimeter and cassette | 14 mm and 10 mm bases | Blocks natural light from contributing to readings |

Optimisation of Extraction of Virus from Plant Material.

A supply of CSSV infected and non-infected *Theobroma cocoa* plants was established from Reading university and were housed in the Envirotron at UWE. A range of buffers and methods of extraction were evaluated using qPCR to determine success.

Method of Extraction from Leaves

The leaves were harvested from CSSV infected and uninfected cocoa plants and roughly chopped with scissors into 0.5 cm pieces. 60 mg leaf tissue was weighed and placed in a 7 ml bijoux or Eppendorf tube containing 10×4 mm ball bearings and 2 ml 0.1M Phosphate buffer, pH 7.2. The vessel was shaken for approximately 2 minutes. The solution was passed through a sieve layer with a minimum pore size 0.1 um and collected. The solid dry plant tissue retained by the sieve layer was discarded and ball bearings recovered and washed. The plant sample was then added to the biosensor.

A table showing the effect of different amounts of leaf tissue, size of ball bearings and volume of buffer is shown in FIG. 5.

Method of TaqMan qPCR

Leaf tissue was extracted in on the day of collection and DNA purified immediately from a 20 µl sample using Qiagen Plant Dneasy mini kit. The kit was used following the manufactures instructions but omitted the RNAse treatment step and eluted sample twice in the same 100 µl buffer at the end to enrich. Samples were stored at −20° C. until use.

TaqMan qPCR was then performed on the DNA samples using a CSSV primer/probe and a plant genomic probe and the Sensifast No RoxMaster Mix (Bioline Cat. BIO-98005). All samples were run in triplicate.

The CSSV and plant genomic probe/primer mix comprised of:

2.5 µl (100 µM) probe

10 µl (100 µM) forward primer

10 µl (100 µM) forward primer 77.5 µl elution buffer (Qiagen)

CSSV ORF3 primers and probe
F-74:
(SEQ ID NO: 32)
5'-CTGAAGCGAGTAGGCAACAA-3'

R-151:
(SEQ ID NO: 33)
5'-CAGTCCAAGGGATGGACTCT-3'

P-129:
(SEQ ID NO: 34)
5'-TCCATCAGGTTGCCATGGCA-3' (5'Fam-3'Tamra)

Primers & probe for nuclear marker in flanking region of single copy T. cacao microsatellite marker mTcCIR25
F-mTcCIR25:
(SEQ ID NO: 35)
5'-CAGATAAGGAAAGGTGGAGTTTGG-3'

R-mTcCIR25:
(SEQ ID NO: 36)
5'-CAAGAATGTCTCCTACATTCACTACG-3'

P-mTcCIR25:
(SEQ ID NO: 37)
5'-TTCCCGTAAGCTTCGTCCCAGATGC-3' (5'Fam-3'Tamra).

Each PCR reaction comprised of: 0.8 µl probe/primer mix
10 µl Mastermix (Bioline)
4.2 µl nuclease free water
5 µl DNA The reactions were run on a Rotor Gene Q instrument. Hold 95° 5', Cycle: 95° C. 10 s (acquiring to cycling A), 60° C. 45 s (acquiring to cycling B). Cycle is repeated 60 times.

The number of CSSV copies were determined in each sample by comparison to a synthetic CSSV references DNA oligomer of know copy number and the CSSV copy number per cell was estimated from the ratio of CSSV copy to plant cell copy number.

Assay Development

Evaluation of the Interaction of Recombinant Antigen CSSV-CP-01 and Recombinant Antibodies.

Testing of *Theobroma cacoa* Plant Samples/Extracts by Competitive ELISA

Materials:
- Coating buffer: 0.1M sodium carbonate buffer pH 8.6
- Sodium carbonate MW 106, so 1.06 g/100 mis dH2O
- Sodium hydrogen carbonate MW 84.01, so 0.86 g/100 mis dH2O, Mix to pH 8.6
- Blocking buffer PBS, 1% Bovine serum albumin (Sigma A7030, #SLBL4277V)
- Wash buffer (PBS, 0.05% tween 20)
- Antibody dilution buffer (PBS, 0.05% tween 20, 0.1% BSA)
- Tetra methylbenzidine Liquid Substrate (Thermo)
- Microlon high binding plate (Greiner 655061)
- CSSVP-CP-01 recombinant fusion protein—Coating concentration 1 to 10 μg/ml Recombinant Reagents

- Goat anti Human IgG F(ab')2:HRP (Bio-Rad STAR126P)
- AbD31998.1 anti-CSSV antibody (BioRad) final concentration 50 ng/ml Plant Samples:

- Leaves were harvested from *Theobroma cacao* plants in the museum collection at CRIG, Ghana and roughly chopped with scissors into 0.5 cm pieces. 60 mg Leaf tissue was weighed and placed in a 7 ml bijoux or Eppendorf tube containing 10×4 mm ball bearings and 2 mls of 0.1M Phosphate buffer B pH7.2 was added and the vessel shaken for approximately 5 minutes.

Procedure:

1. Allow all reagents to reach room temperature before use. Mix all liquids gently prior to use.
2. Prepare CSSVP-CP-01 Antigen, diluted to 1-10 μg/ml in coating buffer.
3. Take immunoassay plate. Add 50 μl of prepared solution to wells. Cover plate and Incubate at 4° C. for 18 hours in a humid box.
4. Decant samples and discard. Wash wells 3 times in Wash buffer using a squirt bottle. Tap plate gently on tissue following every wash to remove all liquid.
5. Fill the wells with 200 μl Blocking buffer. Incubate at room temperature for 2 hours.
6. Prepare recombinant monoclonal antibody at 200 ng/ml in antibody dilution buffer ie. at 2× final concentration.
7. Prepare competing moieties at 2× final concentration in antibody dilution buffer:
   i. Plant sample at 1/5
   ii. Plant sample at 1/50
   iii. Plant sample at 1/500
   Recombinant antigen at 1.25 and 0 μg/ml.
   Equal volumes of antibody and competing recombinant antigen, plant extract or buffer were mixed in an Eppendorf tube and incubated for 30 mins at room temperature.
8. Decant blocking buffer and discard. Wash wells 4 times in Wash buffer. Add 50 μl of primary antibody/competitor to appropriate well. Cover plate and incubate at room temperature for 60 minutes.
9. Wash wells 5 times in Wash buffer.
10. Add 50 μl of secondary antibody Goat anti Human IgG F(ab')2:HRP at 1/2500 in antibody dilution buffer to each well. Cover plate and incubate at room temperature for 60 minutes.
11. Wash wells 5 times in Wash buffer.
12. Add 100 μl 3,3',5,5'-Tetramethylbenzidine Liquid Substrate to the wells. Incubate for 10 minutes at room temperature in the dark.
13. Add 100 μl 1M Sulphuric Acid
14. Read absorbance of wells at 450 nm in a microtitre plate reader Evaluation of Candidate Recombinant Monoclonal Antibodies Fifteen candidate monoclonal antibodies were supplied and evaluated for their ability to bind to recombinant antigen by ELISA (see FIG. 7A). A competitive ELISA was then performed with CSSV positive and negative leaf samples (see FIG. 7B). Candidate antibodies were selected for biotinylation based on results with leaf extracts. Antibodies that bound to CSSV-CP-01 antigen that were competed by CSSV positive leaf extracts, but not by CSSV negative leaf extracts were identified. Recombinant antibodies were selected for biotinylation and used in the Biosensor development including AbD31024.2, AbD31988.1, AbD31999.1 and AbD31998.1.

The results of replicate ELISA experiments for the selected antibodies, across a range of plant extract dilutions are shown in Tables 3 and FIGS. 8 and 9. A strong reproducible dose response was shown by all antibodies. A summary of the selectivity and specificity of each candidate recombinant monoclonal antibody is shown in Table 4.

TABLE 3

Competitive ELISA results of qPCR confirmed CSSV infected plant samples and binding of recombinant antigen and recombinant monoclonal antibodies.

| | Percentage Inhibition % | | | | | |
|---|---|---|---|---|---|---|
| Competitor rAntibody | AbD31024.2 | AbD31025.2 | AbD31988.1 | AbD31994.1 | AbD31999.1 | No Primary control |
| Rec. Antigen | 24 | −4.5 | 38.9 | 26.3 | 11.7 | 2.9 |
| Pos extract 1/1000 | 5.3 | −12.4 | 15.9 | 5.0 | 40.8 | 1.8 |
| Pos extract 1/100 | 16.3 | −12.4 | 46.9 | 5.0 | 69.1 | 12.3 |
| Pos extract 1/10 | 70.1 | −19.8 | 85.2 | 19.5 | 78.5 | 17.8 |
| Neg extract 1/1000 | −3.8 | −32.4 | −1.6 | 0.99 | −2.7 | 14.9 |

TABLE 3-continued Competitive ELISA results of qPCR confirmed CSSV infected plant samples
and binding of recombinant antigen and recombinant monoclonal antibodies.

| | Percentage Inhibition % | | | | | |
|---|---|---|---|---|---|---|
| Competitor rAntibody | AbD31024.2 | AbD31025.2 | AbD31988.1 | AbD31994.1 | AbD31999.1 | No Primary control |
| neg extract 1/100 | −8.2 | −12.1 | −1.7 | 5.0 | −17.5 | 15.9 |
| Neg extract 1/10 | −29 | −42.1 | −42 | 14.6 | −63.9 | 20.3 |

TABLE 4

Summary of the selectivity and specificity of recombinant
monoclonal antibodies binding to CSSV and plant tissue.

| Antibody | Interaction With CSSV-CP-01 | Competition by CSSV Infected plant tissue* | Competition by Non-Infected plant tissue* | Assay Candidate |
|---|---|---|---|---|
| *AbD31024.2* | Y | Y | N | Y |
| AbD31025.2 | Y | N | N | N |
| AbD31986.1 | Y | N | N | N |
| AbD31988.1 | Y | Y | N | Y |
| *AbD31989.1* | Y | Y | N | Y |
| AbD31990.1 | Y | N | N | N |
| AbD31991.1 | Y | N | N | N |
| AbD31992.1 | Y | N | N | N |
| AbD31993.1 | Y | N | N | N |
| AbD31994.1 | Y | Y | Y | N |
| AbD31995.1 | Y | Y | Y | N |
| *AbD31996.1* | Y | Y | N | Y |
| *AbD31997.1* | Y | Y | N | Y |
| AbD31998.1 | Y | Y | N | Y |
| AbD31999.1 | Y | Y | N | Y |

*Above background.
Antibodies highlighted in italics are assay candidates. Antibodies in bold were selected for progression, the amino acid and DNA sequences of antibodies AbD31998.1, AbD31999.1 and AbD31988.1 are shown SEQ ID NOs: 5-31.

Development of Competitive Flow Through Assay—CSSV Biosensor.

The first available biotinylated candidate antibody AbD31024.3 was used in the development of the biosensor in terms of materials, timing, buffers, QDs and detection with the ESElog fluorimeter.

Testing of Plant Samples/Extracts Using the Biosensor

Materials

- MDI membrane 0.8μ CLW-040-SH34 (DL191/3 #LD191917G)
- MDI Absorbent pads AP080 of 24.5 mm×36 mm
- Tesco disposable nappy—absorbent layer
- CSSVP-CP-01 recombinant fusion protein
- AbD31998.5 biotinylated 0.65 mg/ml
- Qdot® 605 nm streptavidin conjugate (life technologies cat. Q10101MP lot #1826419)
- Phosphate buffered saline pH 7.3 (PBS)
- Non-fat dried milk (Marvel)

Method for Biosensor Competition Assay

1. The membrane was placed onto a foil (non-porous) solid support which enabled antibody to be dried to the membrane. The membrane was cut to fit into a cassette and was marked with a pencil so that placement of the dots could be navigated in to the read area. CSSV antigen was diluted in PBS to 100 μg/ml. 10 μls was spotted onto the paper cast Nitrocellulose Membrane of pore size <1 μm and left to air dry at room temperature for 15 mins.
2. The membranes were then blocked in 5% skimmed milk in PBS for 2 hours at room temperature and washed 3 times in PBS. Membranes were stored at 4° C. for 24 hours.
3. Each membrane was assembled onto a stack of 2 MDI Absorbent pads AP080, and a single layer of absorbent material cut to fill the entire area of the cassette.

Biotinylated recombinant monoclonal antibody was diluted to 8 μg/ml in PBS (2× final concentration).

4. Competing test samples were diluted in PBS to 2× final concentration. Plant samples were therefore diluted 1/5, 1/50, 1/500 and 1 μg recombinant antigen was diluted in 100 μl PBS. Sufficient quantities were prepared such that all tests were repeated in triplicate. 100 μl competitor or control PBS was mixed with 100 μl of recombinant monoclonal antibody and left at room temp for 30 mins to pre-incubate prior to assay. All combinations were prepared in triplicate.
5. 200 μl of antibody/competitor was dripped slowly onto the centre of the spot and allowed to flow through.
6. qDots 605 streptavidin conjugate were diluted to 10 nM in PBS and 10 μl was applied and allowed to flow through. This was followed by 2×PBS washes of 500 μl.
7. The fluorescent signal of bound Qdots were measured at an excitation wavelength of 365 nm and emission of 625 nm using the Fluorescence Detector (E1D1) at a distance of 1.4 cm.

Detection of binding of monoclonal antibodies to antigen CSSV-CP-01 using biotinylated antibody AbD31024.3 is shown in FIGS. 10 and 11.

Evaluation of the other candidate recombinant monoclonal antibodies showed AbD31988.5 to give the highest signal and clearest dose response binding to CSSV-CP-01 as shown in FIG. 12. The reduced binding of antibody in the presence of free competing recombinant antigen CSSV-CP-01 is shown in Table 5 and FIGS. 13 and 14. FIG. 16 also shows competition by CSSV positive plant extract.

TABLE 5

CSSV Biosensor results showing competition by two concentrations of competing recombinant antigen CSSV-CP-01 (n = 3)

| Concentration of CSSV-CP1.v1 | Rep 1 | Rep 2 | Rep 3 | Mean | SD | SE | CV |
|---|---|---|---|---|---|---|---|
| 500 ng rec. Ag. | 1575 | 1520 | 1348 | 1481 | 118 | 68 | 8.0 |
| 100 ng rec. Ag. | 1874 | 2214 | 1859 | 1982 | 200 | 116 | 10 |
| No competition | 2500 | 1954 | 2500 | 2318 | 315 | 182 | 14 |

A compilation of three separate Biosensor experiments is shown in Tables 6-8. The results shown are the competition observed by recombinant antigen in three separate experiments using two different batches of CSSV-CP-01a and CSSV-CP-01b.

TABLE 6

CSSV Biosensor results showing competition by recombinant antigen in three separate experiments using two different batches of CSSV-CP-01a, b (n = 3 in each experiment)

| | Fluorescent signal | | | | | | |
|---|---|---|---|---|---|---|---|
| Sample | 1 | 2 | 3 | Mean | SD | SE | CV |
| 500 ng rec. Ag. CSSV-CP-01b | 1570 | 1360 | 1592 | 1507 | 128 | 42 | 8.4 |
| No competition | 1516 | 2005 | 2378 | 1966 | 432 | 144 | 21.9 |
| Background | 1008 | 1103 | 1134 | 1081 | 65 | 21 | 6 |

TABLE 7

UWE, CSSV-CP-01a, CSSV positive plant extract n = 3, QDots - 705 nm

| | Fluorescent signal | | | | | | |
|---|---|---|---|---|---|---|---|
| Sample | Rep 1 | Rep 2 | Rep 3 | Mean | SD | SE | CV |
| Positive extract 1/20 | 337 | 298 | 330 | 321 | 20 | 12 | 6.5 |
| 500 ng rec. Ag. CSSV-CP-01a | 364 | 353 | 360 | 359 | 5.5 | 3.2 | 1.5 |
| No competitor | 441 | 482 | 426 | 449 | 28.9 | 16.8 | 6.4 |

TABLE 8

Competitive Flow through assay to demonstrate competition by CSSV-CP-01a antigen n = 3, QDots - 605 nm

| Concentration of CSSV-CP1.v1 | Rep 1 | Rep 2 | Rep 3 | Mean | SD | SE | CV |
|---|---|---|---|---|---|---|---|
| 1000 ng rec. Ag. | 2115 | 2175 | 1573 | 1954 | 331 | 191 | 16.9 |
| 500 ng rec. Ag. | 1575 | 1520 | 1348 | 1481 | 118 | 68 | 7.9 |
| 100 ng rec. Ag. | 1874 | 2214 | 1859 | 1982 | 200 | 116 | 10.1 |
| No competition | 2500 | 1954 | 2500 | 2318 | 315 | 182 | 13.5 |

Report on the Evaluation of Reagents and Immunoassays to Detect Cocoa Swollen Shoot Virus (CSSV) at the Cocoa Research Centre of Ghana (CRIG).

Day 1. Familiarisation with laboratories, unpack reagents and materials, stage 1 of ELISA.

Day 2. Collection of leaf samples 1-15 from museum collection at CRIG includes three strains of CSSV, New Juaben, Kpeve and Nsaba. All samples collected were photographed (not shown).

Uninfected plants samples A-D, were collected from a different part of the CRIG compound.

An accurate amount of each sample was weighed and the leaf tissue extracted. Plant extracts were stored at 4° C.

The ELISA assay was completed on 15 plant extracts, 1-15 and 4 CSSV negative plant extracts, A-D. Competing recombinant antigen was included as a control.

Day 3. Biosensor assay completed on ×15 plant extracts, 1-15 and ×4 CSSV negative plant extracts, A-D. Competing recombinant antigen at was included as a control.

Results and Discussion

Results of the competitive ELISA for CSSV are shown in Tables 9 and 10 (n=3). No plate reader was available at CRIG to measure absorbance, therefore the results were determined by eye by two people. Photographs are available and results will be analysed using image analysis.

TABLE 9

Competitive ELISA results with a range of CSSV positive and negative plant samples

| Sample Number | Description of Sample | 1 in 10 | 1 in 100 | 1 in 1000 |
|---|---|---|---|---|
| 1 | New Juaben 1A (Seedling) | PP | P | Neg |
| 2 | NSABA (Mature plant, young leaf) | PP | P | Neg |
| 3 | KPEVE | PP | P | Neg |
| 4 | KPEVE | P | Neg | Neg |
| 5 | New Juaben 1A (Seedling) | P | Neg | Neg |
| 6 | New Juaben 1A (Seedling) | P | Neg | Neg |
| 7 | New Juaben 1A (Seedling) | P | Neg | Neg |
| 8 | New Juaben 1A (Mature plant, young leaf) | PP | Neg | Neg |
| 9 | New Juaben 1A (Mature plant, young leaf) | P | Neg | Neg |
| 10 | New Juaben 1A (Mature plant, young leaf) | PPP | P | Neg |
| 11 | New Juaben 1A (Mature plant, red leaf) | Neg | Neg | Neg |
| 12 | KPEVE | P | Neg | Neg |
| 14 | NSABA (Mature plant, young leaf) | Neg | Neg | Neg |
| 15 | NSABA (Mature plant, new flush leaf) | P | Neg | Neg |
| 16 | A | Neg | Neg | Neg |
| 17 | B | (P) | (P) | (P) |
| 18 | C | Neg | Neg | Neg |
| 19 | D | (P) | Neg | Neg |

TABLE 10

Competitive ELISA results with 500 ng of recombinant antigen CSSV-CP-01

| | Concentration (ng/ml) | | | | | |
|---|---|---|---|---|---|---|
| Sample | 4.5 | 1.5 | 1 | 0.3 | 0.1 | 0 |
| Recombinant antigen | PP | PP | PP | PP | P | Neg |

Key: Negative Neg; Strong positives P, PP and PPP; Very weak positive (P)

The results show that 14 out of 15 plant leaf samples were positive for CSSV at a 1:10 to 1:100 dilution, no samples were positive for CSSV at 1:1000 dilution. The assay was able to detect CSSV infection by three strains of CSSV, New Juaben, KPEVE and NSABA. The Ghanaian ELISA assay only detects New Juaben. There were no convincing positives among the CSSV negative plant samples tested.

Subsequent laboratory QPCR results on the above samples have revealed that samples 1-15 contained CSSV. Melt analysis revealed two populations the New Juaben samples formed one group and the other strains formed another.

TABLE 11

| Sample | 1 | 2 | 3 | Mean | SD | SE | CV |
|---|---|---|---|---|---|---|---|
| *Antigen competition* | *1570* | *1360* | *1592* | *1507* | *128* | *42* | *8.4* |
| *No competition* | *1516* | *2005* | *2378* | *1966* | *432* | *144* | *21.9* |
| *Background* | *1008* | *1103* | *1134* | *1081* | *65* | *21* | *6* |
| Sample 10 CSSV positive | 1187 | 1305 | 1228 | 1240 | 59 | 19 | 4.8 |

Figures 16, 17:
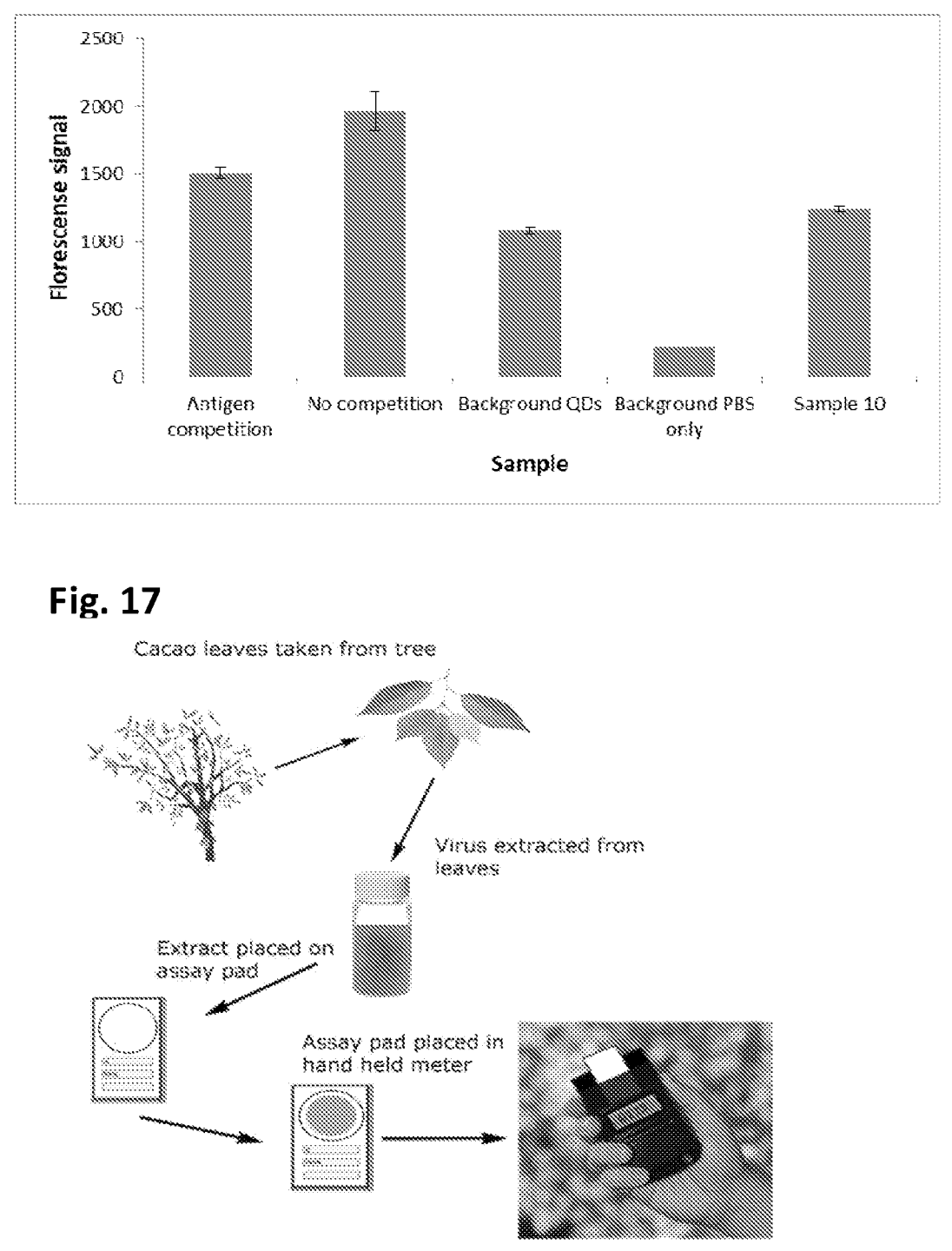

The CSSV biosensor controls (italics) and a CSSV positive Sample 10. in Table 11 show that the Biosensor worked, and are illustrated in FIG. 16.

A conceptual diagram of how the CSSV biosensor detection system will be used in the field is shown in FIG. 17.

Example 2

Objectives:
Validate recombinant antibody Ab 31998.1 in the competitive ELISA with CSSV antigen 1 (CSSV-CP-01) with CSSV infected symptomatic, CSSV non-symptomatic and CSSV non-infected plant extracts.
Compare competitive CSSV ELISA results with the number of CSSV DNA copies/plant cell present in each sample.
Evaluate 3 antibodies: AbD31998.1, AbD31988.1 and AbD31999.1 in the CSSV competitive ELISA to CSSV-CP-01 antigen competition.
Compare the binding of 15 recombinant monoclonal antibodies to CSSV antigen 1 (CSSV-CP-01) and CSSV antigen 2 (CSSV-CP-02).

Results:
CSSV Taqman QPCR
A good dose response was observed for $10^2$-$10^5$ copies of synthetic CSSV DNA (data not shown).

Summary of qPCR Data
CSSV infected plants—$10^4$ to $10^5$ CSSV DNA copies detected.
CSSV infected non-symptomatic plants—$10^2$ to $10^3$ CSSV DNA copies detected.
Uninfected plants—<50 CSSV DNA copies detected.

These data were normalised with plant DNA detected to determine the number of copies of CSSV DNA present per plant cell. This allows for differences in the success of DNA extraction to be accounted for.

Summary of qPCR Data of Plant Leaf Extracts from 'CSSV Infected' *Theombroma cacoa* Plants

TABLE 12

Symptomatic leaves contain 333.5-6.4 CSSV copies/cell; Non-symptomatic leaves contain 1.9-0.1 CSSV copies/cell.

| Plant G6 | Copies/cell | Plant G46 | Copies/cell |
|---|---|---|---|
| Symptomatic | | | |
| Sample 25 | 7.9 | Sample 7 | 67.8 |
| Sample 26 | 6.4 | Sample 22 | 333.5 |
| Sample 27 | 254.6 | Sample 23 | 100.2 |
| Sample 28 | 16.6 | Sample 24 | 298.8 |
| Non-symptomatic | | | |
| Sample 20 | 1 | Sample 8 | 0.4 |
| Sample 30 | 0.2 | Sample 19 | 0.2 |
| Sample 32 | 0.1 | Sample 21 | 1.9 |
| Sample 32 | 0.4 | Sample 29 | 0.9 |

Summary of qPCR Data of Plant Leaf Extracts from 'Uninfected' *Theobroma cacoa* Plants 0.3-0.1 CSSV Copies/Cell

TABLE 13

Uninfected leaves contain 0.6-0.1 CSSV copies/cell (mean = 0.24)

| Plant AM2 | Copies/cell | Plant AM4 | Copies/cell | Plant AM6 | Copies/cell |
|---|---|---|---|---|---|
| Negative | | | | | |
| Sample 11 | 0.2 | Sample 15 | 0.1 | Sample 33 | 0.1 |
| Sample 12 | 0.1 | Sample 15 | 0.2 | Sample 34 | 0.6 |
| Sample 13 | 0.3 | | | Sample 35 | 0.1 |
| Sample 14 | 0.2 | | | Sample 36 | 0.3 |

| | Plant AM5 | Copies/cell |
|---|---|---|
| | Sample 17 | 0.3 |
| | Sample 18 | 0.2 |

Therefore from this experiment any sample containing >0.4 CSSV copies/cell is positive for CSSV.

Figures 18, 19A, 19B:
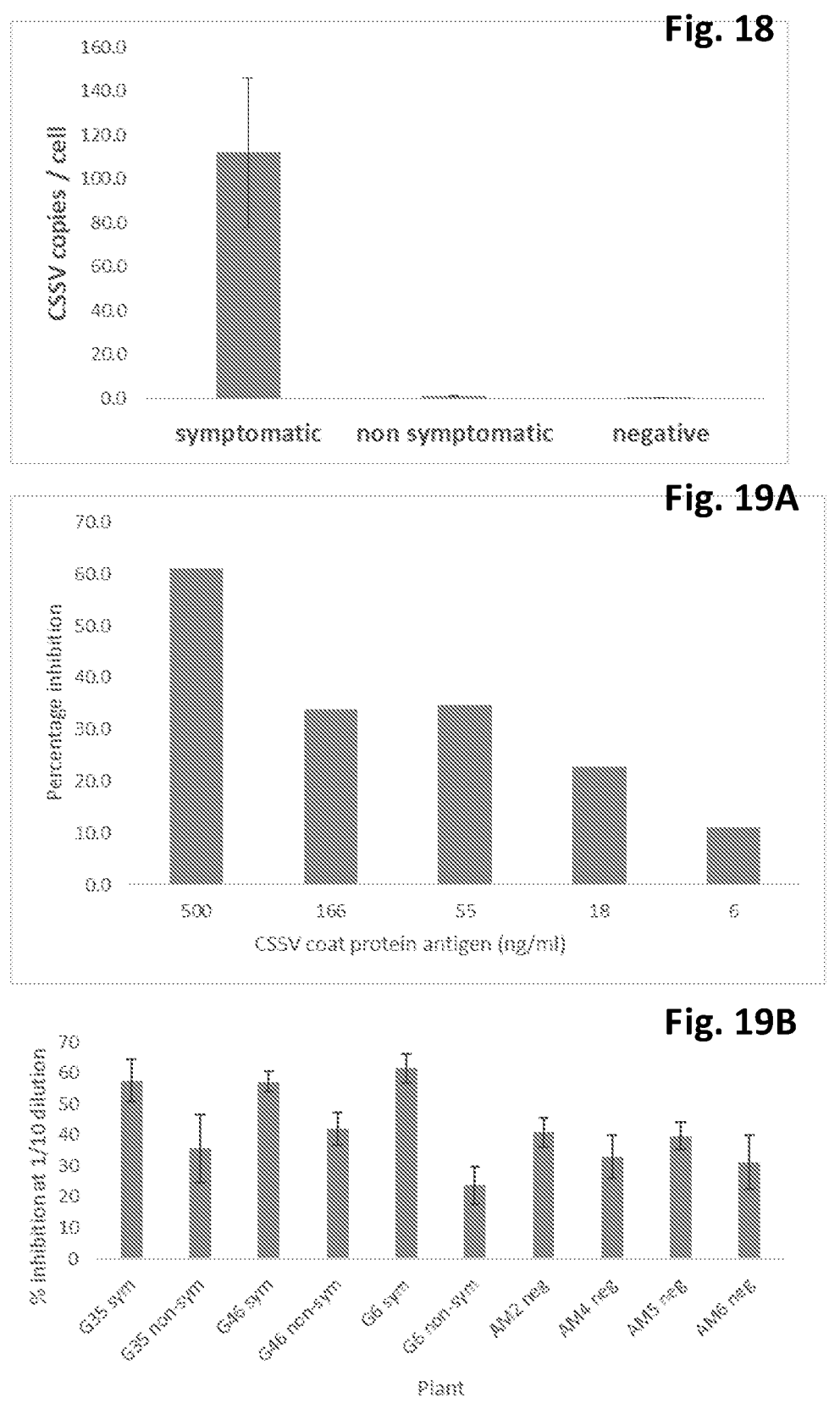

The mean data for these values are displayed in FIG. 18. Validation of Reagents in the CSSV Competitive ELISA and Ability of the Assay to Detect CSSV in Plant Extracts.

FIGS. 19A and 19B represent summary data of the ELISA assays performed. FIG. 19A shows a dose response of CSSV recombinant coat protein. FIG. 19B shows the mean and SE of multiple leaves taken from the same plant.

Figure 20:
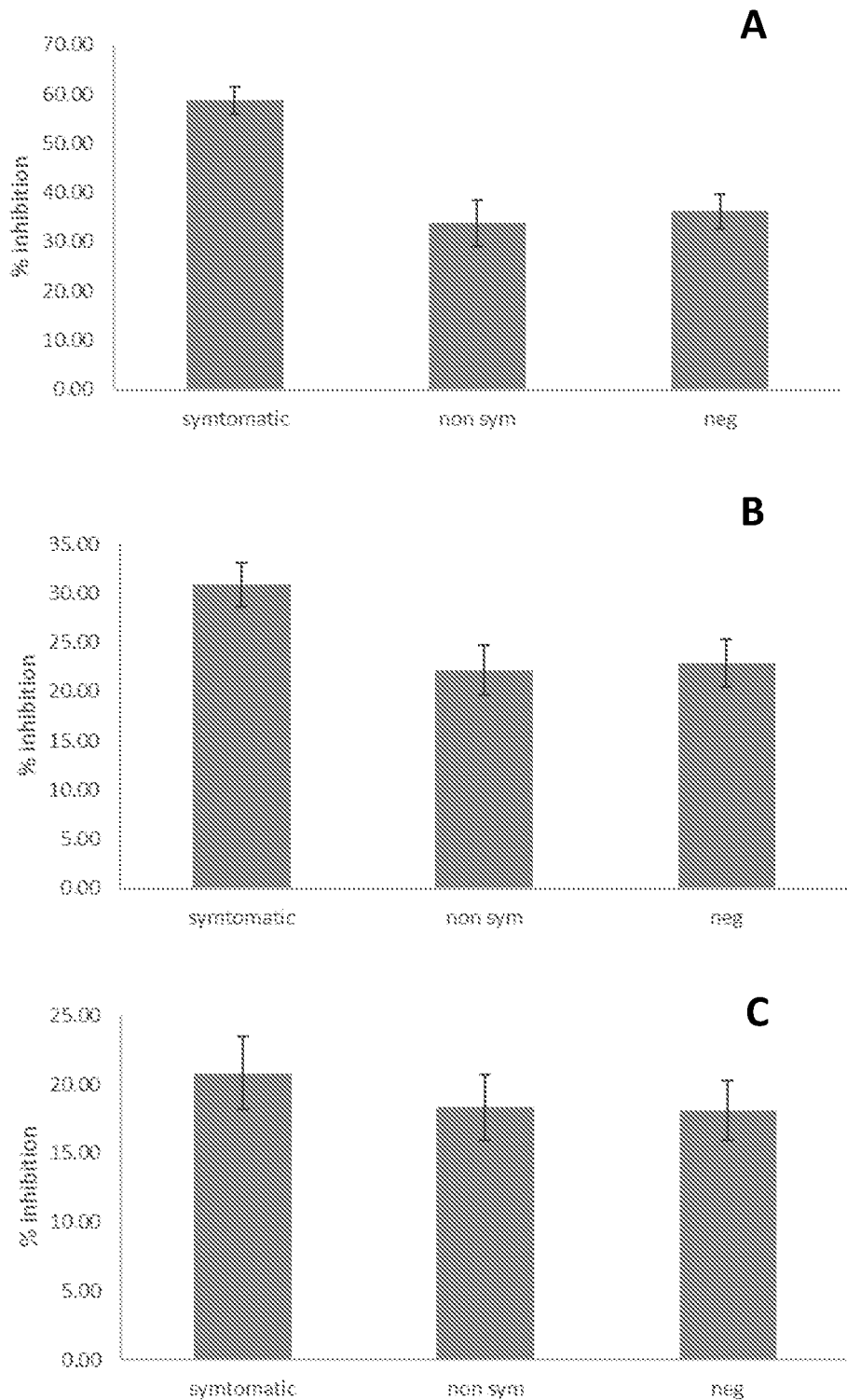
FIG. 20 shows competitive ELISA results using AbD31998.1 at three plant sample dilutions: A % inhibition of CSSV ELISA using samples at 1/10 concentration; B % inhibition of CSSV ELISA using samples at 1/100 concentration; and C % inhibition of CSSV ELISA using samples at 1/1000 concentration.

Competitive ELISA using antibody AbD31998.1 shows results at three plant sample dilutions: 1/10 (FIG. 20A); 1/100 (FIG. 20B); and 1/1000 (FIG. 20C).

CSSV competitive ELISA and Taqman qPCR results for individual infected CSSV plant extracts are shown in FIG. 21. All samples with >45% inhibition in the CSSV competition ELISA had ≥0.4 CSSV DNA copies/cell. These samples are marked as positive for CSSV.

TABLE 14

CSSV competitive ELISA and Taqman qPCR results for individual non-infected plant extracts.

| Sample | Plant | Dilution | % inhibition | Copies/cell |
|---|---|---|---|---|
| 11 | AM2 neg A | 1/10 | 42.6 | 0.2 |
| | | 1/100 | 36.9 | |
| | | 1/1000 | 31.4 | |
| 12 | AM2 neg B | 1/10 | 53.4 | 0.1 |
| | | 1/100 | 30.2 | |
| | | 1/1000 | 19.9 | |
| 13 | AM2 neg C | 1/10 | 34.3 | 0.3 |
| | | 1/100 | 32 | |
| | | 1/1000 | 19.375 | |
| 14 | AM2 neg D | 1/10 | 33.1 | 0.2 |
| | | 1/100 | 12.5 | |
| | | 1/1000 | 19.5 | |
| 15 | AM4 neg A | 1/10 | 26 | 0.1 |
| | | 1/100 | 10.4 | |
| | | 1/1000 | 6.4 | |
| 16 | AM4 neg B | 1/10 | 40 | 0.2 |
| | | 1/100 | 28.7 | |
| | | 1/1000 | 23.7 | |
| 17 | AM5 neg A | 1/10 | 35.2 | 0.3 |
| | | 1/100 | 22.5 | |
| | | 1/1000 | 19.5 | |
| 18 | AM5 neg B | 1/10 | 44.1 | 0.2 |
| | | 1/100 | 28.9 | |
| | | 1/1000 | 28.5 | |
| 33 | AM6 neg A | 1/10 | 5.8 | 0.1 |
| | | 1/100 | 18.6 | |
| | | 1/1000 | 11.1 | |

TABLE 14-continued

CSSV competitive ELISA and Taqman qPCR results
for individual non-infected plant extracts.

| Sample | Plant | Dilution | % inhibition | Copies/cell |
|---|---|---|---|---|
| 34 | AM6 neg B | 1/10 | 45.5 | 0.6 |
| | | 1/100 | 16.2 | |
| | | 1/1000 | 10 | |
| 35 | AM6 neg C | 1/10 | 37.4 | 0.1 |
| | | 1/100 | 19.8 | |
| | | 1/1000 | 16.1 | |
| 36 | AM6 neg D | 1/10 | 36.1 | 0.3 |
| | | 1/100 | 16.8 | |
| | | 1/1000 | 10.8 | |

2/12 CSSV non-infected plants had >45% inhibition in the ELISA, indicating some interference at the highest concentration tested (bold). However, one of those samples also had a qPCR result of ≥0.4 CSSV DNA copies/cell indicating a genuine CSSV positive.

Figures 22, 23:
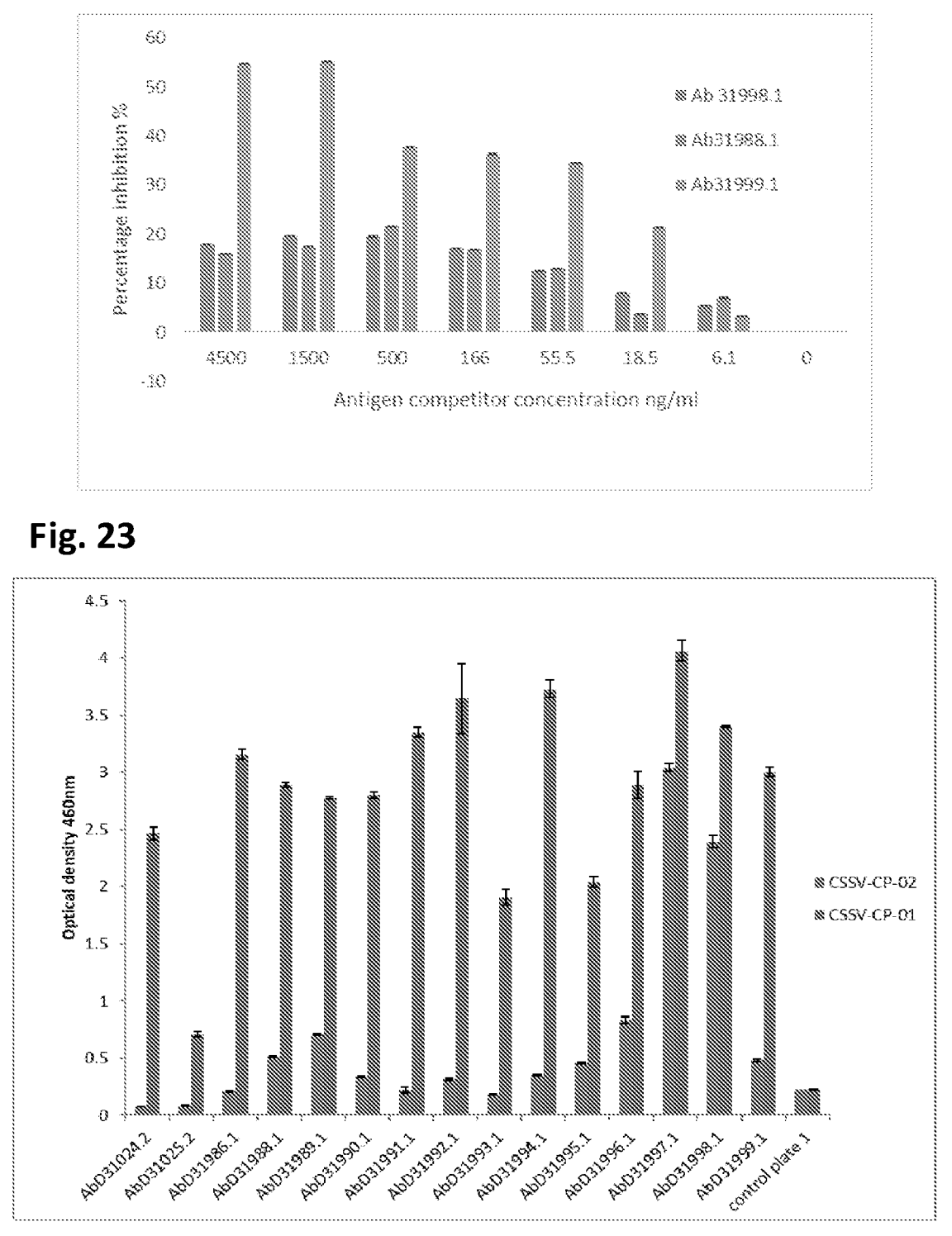

Three anti-CSSV recombinant antibodies (Ab 31998.1, Ab 31988.1 and Ab 31999.1) were compared by competitive ELISA at 1.25 μg/ml of CSSV antigen 1 (CSSV-CP-01) (FIG. 22). The observed antibody sensitivity to competition by CSSV-CP-01 was Ab31999>Ab31998>Ab 31988.

The interaction of the recombinant monoclonal antibodies with CSSV-CP-01 and CSSV-CP-02 was compared (FIG. 23). Antibodies AbD31997.1 and AbD31998.1 interacted strongly with both antigens CSSV-CP-01 and CSSV-CP-02.

Summary of Results
  Validate Recombinant Antibody Ab 31998.1 in the Competitive ELISA with CSSV Antigen 1 (CSSV-CP-01)
Using the Criteria of >45% Inhibition in the ELISA as being Positive for CSSV:
  11/12 symptomatic leaf samples were positive
  5/12 non symptomatic leaf samples were positive
  2/12 uninfected plant samples were positive
  Only 1 of the uninfected samples was confirmed as true CSSV positive i.e. >0.4 copies/cells by qPCR, therefore 1 false positive was observed
  Evaluate and Compare 3 Antibodies AbD31998.1, AbD31988.1 and AbD31999.1
  Antibody sensitivity Ab31999>Ab31998>Ab31988
  Evaluate Binding of 15 Antibodies to CSSV Antigen 1 and CSSV Antigen 2 (CSSV-CP-02)

All antibodies tested were originally selected for interaction with CSSV-CP-01. Antibodies AbD31997.1 and AbD31998.1 were found to have the highest binding with both antigens.

Antibody AbD31998.1 has previously been shown to be the most sensitive to competition.

CONCLUSION

The Taqman qPCR has supported the results obtained in the CSSV competitive ELISA in that those plants with detectable levels of CSSV above 0.4 copies/cell were also positive in the competitive ELISA. For two out of three plants tested, CSSV was detected in symptomatic and >50% non-symptomatic leaves. These results were obtained with CSSV-CP-01 and antibody AbD31998.

Experiments have determined that antibody Ab31999 has greater sensitivity when tested with CSSV-CP-01.

Antigen CSSV-CP-02 was produced using sequences from currently circulating strains of CSSV in Ghana and the Cote D'Ivoire; the antibody AbD31998 is also the antibody that binds strongly to both antigens.

REFERENCES

H. Dzahini-Obiatey and R. T. V. Fox (2010). African Journal of Biotechnology Vol. 9 (5), pp. 593-603,
Muller, E., Jacquot, E., Yot, P. Journal of Virological Methods (2001) 93:15-22
Oro, F., Mississo, E., Okassa, M. et al. Arch Virol (2012) 157: 509.
Chingandu, N., Kouakou, K., Aka, R., Ameyaw, G., Gutierrez, O. A., Herrmann H. W., and Brown, J. K. Virology Journal (2017) 14:199.
Muller, E., Ravel, S., Agret, C., Abrokwah. F., Dzahini-Obiatey, H., Galyuon, I., Kouakou, K., Jeyaseelan, E. C., Allainguillaume, J., Wetten, A. Virus Res. 2018 Jan. 15; 244:235-251 Epub 2017 Nov. 21
Fernandez-Jaramillo, A. A., Duarte-Galvan. C., Contreras-Medina, L. M., Torres-Pacheco, I., de J. Romero-Troncoso, R., Guevara-Gonzalez, R. G and Millan-Almaraz, R. J. 2012 Instrumentation in Developing Chlorophyll Fluorescence Biosensing: A Review. Sensors, 12, 11853-11869

The invention claimed is:

1. A method for detecting Cocoa Swollen Shoot Virus (CSSV) using a porous membrane based sensor, the sensor comprising at least one recombinant CSSV coat protein antigen having at least 80% sequence identity to the amino acid sequence of SEQ ID NO: 2 or 4, the method comprising the steps of:
   (i) contacting cocoa plant material with a labelled binding reagent that specifically binds to the recombinant coat protein antigen to produce a mixture comprising the plant material and binding reagent; and
   (ii) contacting the mixture with the membrane based sensor,
   wherein the binding reagent is a monoclonal antibody comprising:
      a) a heavy chain CDR1 of SEQ ID NO:17, a heavy chain CDR2 of SEQ ID NO: 18, a heavy chain CDR3 of SEQ ID NO: 19, a light chain CDR1 of SEQ ID NO:20, a light chain CDR2 of SEQ ID NO:21, and a light chain CDR3 of SEQ ID NO:22; or
      b) a heavy chain CDR1 of SEQ ID NO:26, a heavy chain CDR2 of SEQ ID NO: 27, a heavy chain CDR3 of SEQ ID NO:28, a light chain CDR1 of SEQ ID NO:29, a light chain CDR2 of SEQ ID NO:30, and a light chain CDR3 of SEQ ID NO:31.

2. The method according to claim 1, wherein the label is a fluorescent label.

3. The method claim 1, wherein the label is a quantum dot having an emission wavelength of at least 600 nm.

4. The method according to claim 1, wherein the cocoa plant material is leaf material and/or stem material.

5. The method according to claim 1, wherein the monoclonal antibody is a F(ab)2 fragment.

6. The method according to claim 1, wherein the sensor comprises a sieve layer in the form of a superficial layer of membrane having a pore size of at least 1 μm.

7. The method according to claim 1, wherein the sensor comprises a capture layer in the form of a porous membrane layer in which the at least one recombinant CSSV coat protein antigen is immobilised.

8. The method according to claim 7, wherein the sensor comprises a sink layer in the form of an absorbent layer near the capture layer.

9. The method according to claim 8, wherein the sensor comprises a blocking layer in the form of a porous non-reflective layer between the capture layer and the sink layer.

10. An assay for detecting a viral infection in a plant, the assay comprising the steps of:
    contacting plant material with a labelled recombinant binding reagent that specifically binds to a viral coat protein antigen to produce a mixture comprising the plant material and binding reagent;
    contacting the mixture with viral coat protein antigen which is immobilised in or on a surface;
    removing labelled recombinant binding reagent that is not bound to the immobilised viral coat protein antigen; and
    detecting the presence of the remaining labelled recombinant binding reagent to determine the presence or absence of the viral infection,
    wherein the viral infection is a Cocoa Swollen Shoot Virus (CSSV) infection,
    wherein the binding reagent is a monoclonal antibody comprising:
       a) a heavy chain CDR1 of SEQ ID NO: 17, a heavy chain CDR2 of SEQ ID NO: 18, a heavy chain CDR3 of SEQ ID NO: 19, a light chain CDR1 of SEQ ID NO:20, a light chain CDR2 of SEQ ID NO:21, and a light chain CDR3 of SEQ ID NO:22; or
       b) a heavy chain CDR1 of SEQ ID NO:26, a heavy chain CDR2 of SEQ ID NO: 27, a heavy chain CDR3 of SEQ ID NO:28, a light chain CDR1 of SEQ ID NO:29, a light chain CDR2 of SEQ ID NO:30, and a light chain CDR3 of SEQ ID NO:31, and
    wherein the amount of labelled recombinant binding reagent detected is inversely correlated with the number of viral particles present in the plant material.

11. The assay according to claim 10, wherein the viral coat protein antigen is a recombinant antigen.

12. The assay claim 10, wherein the monoclonal antibody is a F(ab)2 fragment.

13. The assay according to claim 10, wherein the label is a quantum dot having an excitation wavelength of at least 600 nm.

14. An isolated binding reagent that specifically binds to a recombinant Cocoa Swollen Shoot Virus (CSSV) coat protein antigen, wherein the binding reagent is a monoclonal antibody comprising:
    a) a heavy chain CDR1 of SEQ ID NO: 17, a heavy chain CDR2 of SEQ ID NO: 18, a heavy chain CDR3 of SEQ ID NO:19, a light chain CDR1 of SEQ ID NO:20, a light chain CDR2 of SEQ ID NO:21, and a light chain CDR3 of SEQ ID NO:22; or
    b) a heavy chain CDR1 of SEQ ID NO:26, a heavy chain CDR2 of SEQ ID NO: 27, a heavy chain CDR3 of SEQ ID NO:28, a light chain CDR1 of SEQ ID NO:29, a light chain CDR2 of SEQ ID NO:30, and a light chain CDR3 of SEQ ID NO:31.

15. The isolated binding reagent according to claim 14, wherein the monoclonal antibody is a F(ab)2 fragment.

16. The isolated binding reagent according to claim 14, wherein the binding reagent is conjugated to a label such as a florescent label.

17. A device comprising a capture layer in the form of a porous membrane layer in which a recombinant CSSV coat protein antigen is immobilised.

18. The device according to claim 17, wherein the device comprises a sieve layer in the form of a superficial layer of membrane having a pore size of at least 1 μm.

19. The device according to claim 17, wherein the device comprises a sink layer in the form of an absorbent layer near the capture layer.

20. The device according to claim 19, wherein the device comprises a blocking layer in the form of a porous non-reflective layer between the capture layer and the sink layer.

* * * * *

SEQUENCE LISTING

```
<160> NUMBER OF SEQ ID NOS: 37

<210> SEQ ID NO 1
<211> LENGTH: 1002
<212> TYPE: DNA
<213> ORGANISM: Artificial Sequence
<220> FEATURE:
<223> OTHER INFORMATION: Recombinant CSSV coat protein antigen 01

<400> SEQUENCE: 1
gttgactata caccacctgg tgacacactg atgacacctg tcggatatcc accggcctcg      60
tcatcaagat caacagtaac aacaccaagt aggcccccctt tatttgaagg aagggttaca     120
cacgtgccaa gattcttaaa acgggatgac tacacagaat ggtggcaact accatcatcc     180
caaggcacaa ctggggcatt atttgtgatg cccaaacaaa taggcctatt tcatgatgtc     240
ttctccagat gggagtccat caccaaaaac tatgttgcgg cccaaagttt cacggaccca     300
```

```
acagaaaaga tggagttcat ggaaaactta cttggagaaa cagaaaaact aacctggatc    360
caatggagaa tgaattatga ggctgagtac cagcagctgt taacccaagc tgatggacgg    420
caagggaccc agaatatctt gtcccaaatt aagagagtct tctctctaga agaccccgcc    480
tcaggatcca cgaggataca agatgctgca tacagagacc ttgaaagatt gacctgccac    540
aacataaaag atatcgttca gttcctgaat gattatgggc ggttagcagc aaaaagtggg    600
cgactgtttc taggaacaga gctcagtgaa aaactatgga tgaagatgcc accagaacta    660
gggaatcgca tgaaggaagc atttcaaaag gaatactcag gcaatgaagt aggagtcttc    720
ccgcgtatct tgttcgcgta cagatactta aacaagaat gcaagatgc agcgtttaag     780 cgcagcctga agtcgttgag tttctgtaag gacatgccgt tgacaggtta ctatgataaa    840
acacccaaat acggcatgag gaagtcaaaa acttacaaag gaaagccaca cgcatcacat    900
gcaagagtag aaaagagaaa gcacttaatc aggaataaaa agtgcaagtg ctatctgtgt    960
ggagatgaag gacatttgc cagagaatgc cctaataaca aa                      1002
```

<210> SEQ ID NO 2
<211> LENGTH: 334
<212> TYPE: PRT
<213> ORGANISM: Artificial Sequence
<220> FEATURE:
<223> OTHER INFORMATION: Recombinant CSSV coat protein antigen 01
      putative amino acid sequence

<400> SEQUENCE: 2

```
Val Asp Tyr Thr Pro Pro Gly Asp Thr Leu Met Thr Pro Val Gly Tyr
1               5                   10                  15

Pro Pro Ala Ser Ser Arg Ser Thr Val Thr Thr Pro Ser Arg Pro
            20                  25                  30

Pro Leu Phe Glu Gly Arg Val Thr His Val Pro Arg Phe Leu Lys Arg
        35                  40                  45

Asp Asp Tyr Thr Glu Trp Trp Gln Leu Pro Ser Ser Gln Gly Thr Thr
50                  55                  60

Gly Ala Leu Phe Val Met Pro Lys Gln Ile Gly Leu Phe His Asp Val
65                  70                  75                  80

Phe Ser Arg Trp Glu Ser Ile Thr Lys Asn Tyr Val Ala Ala Gln Ser
                85                  90                  95

Phe Thr Asp Pro Thr Glu Lys Met Glu Phe Met Glu Asn Leu Leu Gly
            100                 105                 110

Glu Thr Glu Lys Leu Thr Trp Ile Gln Trp Arg Met Asn Tyr Glu Ala
        115                 120                 125

Glu Tyr Gln Gln Leu Leu Thr Gln Ala Asp Gly Arg Gln Gly Thr Gln
130                 135                 140

Asn Ile Leu Ser Gln Ile Lys Arg Val Phe Ser Leu Glu Asp Pro Ala
145                 150                 155                 160

Ser Gly Ser Thr Arg Ile Gln Asp Ala Ala Tyr Arg Asp Leu Glu Arg
                165                 170                 175

Leu Thr Cys His Asn Ile Lys Asp Ile Val Gln Phe Leu Asn Asp Tyr
            180                 185                 190

Gly Arg Leu Ala Ala Lys Ser Gly Arg Leu Phe Leu Gly Thr Glu Leu
        195                 200                 205

Ser Glu Lys Leu Trp Met Lys Met Pro Pro Glu Leu Gly Asn Arg Met
    210                 215                 220

Lys Glu Ala Phe Gln Lys Glu Tyr Ser Gly Asn Glu Val Gly Val Phe
225                 230                 235                 240
```

Pro Arg Ile Leu Phe Ala Tyr Arg Tyr Leu Glu Gln Glu Cys Lys Asp
              245                 250                 255

Ala Ala Phe Lys Arg Ser Leu Lys Ser Leu Ser Phe Cys Lys Asp Met
              260                 265                 270

Pro Leu Thr Gly Tyr Tyr Asp Lys Thr Pro Lys Tyr Gly Met Arg Lys
              275                 280                 285

Ser Lys Thr Tyr Lys Gly Lys Pro His Ala Ser His Ala Arg Val Glu
              290                 295                 300

Lys Arg Lys His Leu Ile Arg Asn Lys Lys Cys Lys Cys Tyr Leu Cys
305                 310                 315                 320

Gly Asp Glu Gly His Phe Ala Arg Glu Cys Pro Asn Asn Lys
              325                 330

<210> SEQ ID NO 3
<211> LENGTH: 990
<212> TYPE: DNA
<213> ORGANISM: Artificial Sequence
<220> FEATURE:
<223> OTHER INFORMATION: recombinant CSSV coat protein antigen 02 DNA
      sequence

<400> SEQUENCE: 3
gttgactaca cacctcctgg agatacgtta atgactccag ttgggtatcc acctgcatca      60
acatctagac aaccacaacc gtctagaccc ccactgtatg agggacgaat ccctcagatt     120
cctagattca gaaaagatga ctacactgaa tggtggcaat tgccatcttc gcaagccaca     180
acaggagcct tatttgttat gccaaagcaa attggcttct tccatgacgt ctttccaga     240
tgggaatcag tcacgaagaa ctacatagct ttgcaggagt tcactgatcc tgctgacaaa     300
gttgaattca tagaaaacct gctgggagaa acagaaaagc taacatggat tcaatggagg     360
atgaactatg tagcagaata tcagcaactg ataacacaag ctgatggaag acaagggaca     420
cagaatatcc tgtcccaaat aaagagaatc ttctctttag aagaccctgc atcagggtct     480
acaaggatac aagatgctgc ttacagagat ctggagagat taacatgcaa caacatcaaa     540
gacatagtcc aattcctgaa tgactatggc agattagcag caaaaactgg cagaatgttc     600
ataagcagag agcttagtga taaactatgg ctcaaaatgc cgccagaact gggaaccaga     660
atgaaggaag cgtatgacaa ggagtaccca ggcaatgacg taggagtata tcccagaata     720
ctctacgcct acaaataccc tggaacaggag tgtaaagacg cagccttcaa agaagtctg     780
aaatctctga gttttctgcag agatatacca atcaccgggt actacgacaa gccaaagtat     840
ggtgtccgga gatccactac atacaaagga aagccacatg caacacatgc aaggattgaa     900
aagaagaaac acctagtcag aaacaaaagg tgtaaatgtt atttatgtgg cgatgaaggc     960
cattttgcta gagaatgccc taatgcaaaa                                     990

<210> SEQ ID NO 4
<211> LENGTH: 330
<212> TYPE: PRT
<213> ORGANISM: Artificial Sequence
<220> FEATURE:
<223> OTHER INFORMATION: recombinant CSSV coat protein antigen 02 -
      putative amino acid sequence

<400> SEQUENCE: 4

Val Asp Tyr Thr Pro Pro Gly Asp Thr Leu Met Thr Pro Val Gly Tyr
1               5                   10                  15

Pro Pro Ala Ser Thr Ser Arg Gln Pro Gln Pro Ser Arg Pro Pro Leu

```
            20                  25                  30
Tyr Glu Gly Arg Ile Pro Gln Ile Pro Arg Phe Arg Lys Asp Asp Tyr
                35                  40                  45

Thr Glu Trp Trp Gln Leu Pro Ser Ser Gln Ala Thr Thr Gly Ala Leu
 50                  55                  60

Phe Val Met Pro Lys Gln Ile Gly Phe Phe His Asp Val Phe Ser Arg
 65                  70                  75                  80

Trp Glu Ser Val Thr Lys Asn Tyr Ile Ala Leu Gln Glu Phe Thr Asp
                85                  90                  95

Pro Ala Asp Lys Val Glu Phe Ile Glu Asn Leu Leu Gly Glu Thr Glu
                100                 105                 110

Lys Leu Thr Trp Ile Gln Trp Arg Met Asn Tyr Val Ala Glu Tyr Gln
                115                 120                 125

Gln Leu Ile Thr Gln Ala Asp Gly Arg Gln Gly Thr Gln Asn Ile Leu
                130                 135                 140

Ser Gln Ile Lys Arg Ile Phe Ser Leu Glu Asp Pro Ala Ser Gly Ser
145                 150                 155                 160

Thr Arg Ile Gln Asp Ala Ala Tyr Arg Asp Leu Glu Arg Leu Thr Cys
                165                 170                 175

Asn Asn Ile Lys Asp Ile Val Gln Phe Leu Asn Asp Tyr Gly Arg Leu
                180                 185                 190

Ala Ala Lys Thr Gly Arg Met Phe Ile Ser Arg Glu Leu Ser Asp Lys
                195                 200                 205

Leu Trp Leu Lys Met Pro Pro Glu Leu Gly Thr Arg Met Lys Glu Ala
                210                 215                 220

Tyr Asp Lys Glu Tyr Pro Gly Asn Asp Val Gly Val Tyr Pro Arg Ile
225                 230                 235                 240

Leu Tyr Ala Tyr Lys Tyr Leu Glu Gln Glu Cys Lys Asp Ala Ala Phe
                245                 250                 255

Lys Arg Ser Leu Lys Ser Leu Ser Phe Cys Arg Asp Ile Pro Ile Thr
                260                 265                 270

Gly Tyr Tyr Asp Lys Pro Lys Tyr Gly Val Arg Arg Ser Thr Thr Tyr
                275                 280                 285

Lys Gly Lys Pro His Ala Thr His Ala Arg Ile Glu Lys Lys His
                290                 295                 300

Leu Val Arg Asn Lys Arg Cys Lys Cys Tyr Leu Cys Gly Asp Glu Gly
305                 310                 315                 320

His Phe Ala Arg Glu Cys Pro Asn Ala Lys
                325                 330

<210> SEQ ID NO 5
<211> LENGTH: 690
<212> TYPE: PRT
<213> ORGANISM: Artificial Sequence
<220> FEATURE:
<223> OTHER INFORMATION: AbD31988 - Amino acid sequence of Fd chain and
      tags

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
                20                  25                  30

Tyr Met Ser Trp Val Arg Gln Ala Pro Gly Gln Gly Leu Glu Trp Met
                35                  40                  45
```

```
Gly Trp Ile Asn Pro Tyr Asn Gly Val Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Glu Asp Thr Ala Val Tyr Tyr Cys
                 85                  90                  95
Ala Arg Gly Leu Gly Ser Gln Phe Asp Tyr Trp Gly Gln Gly Thr Leu
             100                 105                 110
Val Thr Val Ser Ser Ala Ser Thr Lys Gly Pro Ser Val Phe Pro Leu
             115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Glu Phe Lys Ala Glu
210                 215                 220
Met Pro Val Leu Glu Asn Arg Ala Ala Gln Gly Asp Ile Thr Thr Pro
225                 230                 235                 240
Gly Gly Ala Arg Arg Leu Thr Gly Asp Gln Thr Ala Ala Leu Arg Asp
                245                 250                 255
Ser Leu Ser Asp Lys Pro Ala Lys Asn Ile Ile Leu Leu Ile Gly Asp
            260                 265                 270
Gly Met Gly Asp Ser Glu Ile Thr Ala Ala Arg Asn Tyr Ala Glu Gly
            275                 280                 285
Ala Gly Gly Phe Phe Lys Gly Ile Asp Ala Leu Pro Leu Thr Gly Gln
290                 295                 300
Tyr Thr His Tyr Ala Leu Asn Arg Lys Thr Gly Lys Pro Asp Tyr Val
305                 310                 315                 320
Thr Ser Ser Ala Ala Ser Ala Thr Ala Trp Ser Thr Gly Val Lys Thr
                325                 330                 335
Tyr Asn Gly Ala Leu Gly Val Asp Ile His Glu Lys Asp His Pro Thr
            340                 345                 350
Ile Leu Glu Met Ala Lys Ala Ala Gly Leu Ala Thr Gly Asn Val Ser
            355                 360                 365
Thr Ala Glu Leu Gln Asp Ala Thr Pro Ala Ala Leu Val Ala His Val
370                 375                 380
Thr Ser Arg Lys Cys Tyr Gly Pro Ser Ala Thr Ser Glu Lys Cys Pro
385                 390                 395                 400
Gly Asn Ala Leu Glu Lys Gly Gly Lys Gly Ser Ile Thr Glu Gln Leu
                405                 410                 415
Leu Asn Ala Arg Ala Asp Val Thr Leu Gly Gly Gly Ala Lys Thr Phe
            420                 425                 430
Ala Glu Thr Ala Thr Ala Gly Glu Trp Gln Gly Lys Thr Leu Arg Glu
            435                 440                 445
Gln Ala Gln Ala Arg Gly Tyr Gln Leu Val Ser Asp Ala Ala Ser Leu
450                 455                 460
Asn Ser Val Thr Glu Ala Asn Gln Gln Lys Pro Leu Leu Gly Leu Phe
```

```
                465                 470                 475                 480
Ala Asp Gly Asn Met Pro Val Arg Trp Leu Gly Pro Lys Ala Thr Tyr
                    485                 490                 495

His Gly Asn Ile Asp Lys Pro Ala Val Thr Cys Thr Pro Asn Phe Gln
                500                 505                 510

Arg Asn Asp Ser Val Pro Thr Leu Ala Gln Met Thr Asp Lys Ala Ile
                515                 520                 525

Glu Leu Leu Ser Lys Asn Glu Lys Gly Phe Phe Leu Gln Val Glu Gly
                530                 535                 540

Ala Ser Ile Asp Lys Gln Asp His Ala Ala Asn Pro Cys Gly Gln Ile
545                 550                 555                 560

Gly Glu Thr Val Asp Leu Asp Glu Ala Val Gln Arg Ala Leu Glu Phe
                    565                 570                 575

Ala Lys Lys Glu Gly Asn Thr Leu Val Ile Val Thr Ala Asp His Ala
                580                 585                 590

His Ala Ser Gln Ile Val Ala Pro Asp Thr Lys Ala Pro Gly Leu Thr
                595                 600                 605

Gln Ala Leu Asn Thr Lys Asp Gly Ala Val Met Val Met Ser Tyr Gly
610                 615                 620

Asn Ser Glu Glu Asp Ser Gln Glu His Thr Gly Ser Gln Leu Arg Ile
625                 630                 635                 640

Ala Ala Tyr Gly Pro His Ala Ala Asn Val Val Gly Leu Thr Asp Gln
                    645                 650                 655

Thr Asp Leu Phe Tyr Thr Met Lys Ala Ala Leu Gly Leu Lys Gly Ala
                660                 665                 670

Pro Asp Tyr Lys Asp Asp Asp Lys Gly Ala Pro His His His His
                675                 680                 685

His His
    690

<210> SEQ ID NO 6
<211> LENGTH: 221
<212> TYPE: PRT
<213> ORGANISM: Artificial Sequence
<220> FEATURE:
<223> OTHER INFORMATION: AbD31988 heavy chain

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Tyr Phe Asp Ile Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
```

```
                   130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Glu Phe
    210                 215                 220

<210> SEQ ID NO 7
<211> LENGTH: 215
<212> TYPE: PRT
<213> ORGANISM: Artificial Sequence
<220> FEATURE:
<223> OTHER INFORMATION: AbD31988 - light chain

<400> SEQUENCE: 7

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
                20                  25                  30

Ala Val Trp Tyr Gln Gln Leu Pro Gly Thr Ala Pro Lys Leu Leu
                35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Leu Ser Leu
                85                  90                  95

Thr Ser Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
    195                 200                 205

Thr Val Ala Pro Thr Glu Ala
    210                 215

<210> SEQ ID NO 8
<211> LENGTH: 5
<212> TYPE: PRT
<213> ORGANISM: Artificial Sequence
<220> FEATURE:
<223> OTHER INFORMATION: AbD31988 heavy chain CDR1

<400> SEQUENCE: 8
```

Ser Tyr Ala Ile Ser
1               5

<210> SEQ ID NO 9
<211> LENGTH: 17
<212> TYPE: PRT
<213> ORGANISM: Artificial Sequence
<220> FEATURE:
<223> OTHER INFORMATION: AbD31988 heavy chain CDR2

<400> SEQUENCE: 9

Arg Ile Ile Pro Ile Phe Gly Thr Ala Asn Tyr Ala Gln Lys Phe Gln
1               5                   10                  15

Gly

<210> SEQ ID NO 10
<211> LENGTH: 16
<212> TYPE: PRT
<213> ORGANISM: Artificial Sequence
<220> FEATURE:
<223> OTHER INFORMATION: AbD31988 heavy chain CDR3

<400> SEQUENCE: 10

Arg Ile Ile Pro Ile Phe Gly Thr Ala Asn Tyr Ala Gln Lys Phe Gln
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: AbD31988 light chain CDR1

<400> SEQUENCE: 11

Ser Gly Ser Ser Ser Asn Ile Gly Ser Asn Ala Val Trp
1               5                   10

<210> SEQ ID NO 12
<211> LENGTH: 7
<212> TYPE: PRT
<213> ORGANISM: Artificial Sequence
<220> FEATURE:
<223> OTHER INFORMATION: AbD31988 light chain CDR2

<400> SEQUENCE: 12

Asp Asn Asn Lys Arg Pro Ser
1               5

<210> SEQ ID NO 13
<211> LENGTH: 11
<212> TYPE: PRT
<213> ORGANISM: Artificial Sequence
<220> FEATURE:
<223> OTHER INFORMATION: AbD31988 light chain CDR3

<400> SEQUENCE: 13

Gln Ser Trp Asp Leu Ser Leu Thr Ser Tyr Val
1               5                   10

<210> SEQ ID NO 14
<211> LENGTH: 690
<212> TYPE: PRT
<213> ORGANISM: Artificial Sequence
<220> FEATURE:
<223> OTHER INFORMATION: AbD31998 Fd chain and tags

<400> SEQUENCE: 14

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ser Asn Tyr
            20                  25                  30

Tyr Met Ser Trp Val Arg Gln Ala Pro Gly Gln Gly Leu Glu Trp Met
        35                  40                  45

Gly Trp Ile Asn Pro Tyr Asn Gly Val Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Leu Gly Ser Gln Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe Lys Ala Glu
    210                 215                 220

Met Pro Val Leu Glu Asn Arg Ala Ala Gln Gly Asp Ile Thr Thr Pro
225                 230                 235                 240

Gly Gly Ala Arg Arg Leu Thr Gly Asp Gln Thr Ala Ala Leu Arg Asp
                245                 250                 255

Ser Leu Ser Asp Lys Pro Ala Lys Asn Ile Ile Leu Leu Ile Gly Asp
            260                 265                 270

Gly Met Gly Asp Ser Glu Ile Thr Ala Ala Arg Asn Tyr Ala Glu Gly
        275                 280                 285

Ala Gly Gly Phe Phe Lys Gly Ile Asp Ala Leu Pro Leu Thr Gly Gln
    290                 295                 300

Tyr Thr His Tyr Ala Leu Asn Arg Lys Thr Gly Lys Pro Asp Tyr Val
305                 310                 315                 320

Thr Ser Ser Ala Ala Ser Ala Thr Ala Trp Ser Thr Gly Val Lys Thr
                325                 330                 335

Tyr Asn Gly Ala Leu Gly Val Asp Ile His Glu Lys Asp His Pro Thr
            340                 345                 350

Ile Leu Glu Met Ala Lys Ala Ala Gly Leu Ala Thr Gly Asn Val Ser
        355                 360                 365

Thr Ala Glu Leu Gln Asp Ala Thr Pro Ala Ala Leu Val Ala His Val
    370                 375                 380

Thr Ser Arg Lys Cys Tyr Gly Pro Ser Ala Thr Ser Glu Lys Cys Pro
385                 390                 395                 400

Gly Asn Ala Leu Glu Lys Gly Gly Lys Gly Ser Ile Thr Glu Gln Leu
                405                 410                 415
```

-continued

Leu Asn Ala Arg Ala Asp Val Thr Leu Gly Gly Ala Lys Thr Phe
            420                 425                 430

Ala Glu Thr Ala Thr Ala Gly Glu Trp Gln Gly Lys Thr Leu Arg Glu
        435                 440                 445

Gln Ala Gln Ala Arg Gly Tyr Gln Leu Val Ser Asp Ala Ala Ser Leu
    450                 455                 460

Asn Ser Val Thr Glu Ala Asn Gln Gln Lys Pro Leu Leu Gly Leu Phe
465                 470                 475                 480

Ala Asp Gly Asn Met Pro Val Arg Trp Leu Gly Pro Lys Ala Thr Tyr
                485                 490                 495

His Gly Asn Ile Asp Lys Pro Ala Val Thr Cys Thr Pro Asn Pro Gln
            500                 505                 510

Arg Asn Asp Ser Val Pro Thr Leu Ala Gln Met Thr Asp Lys Ala Ile
        515                 520                 525

Glu Leu Leu Ser Lys Asn Glu Lys Gly Phe Phe Leu Gln Val Glu Gly
    530                 535                 540

Ala Ser Ile Asp Lys Gln Asp His Ala Ala Asn Pro Cys Gly Gln Ile
545                 550                 555                 560

Gly Glu Thr Val Asp Leu Asp Glu Ala Val Gln Arg Ala Leu Glu Phe
                565                 570                 575

Ala Lys Lys Glu Gly Asn Thr Leu Val Ile Val Thr Ala Asp His Ala
            580                 585                 590

His Ala Ser Gln Ile Val Ala Pro Asp Thr Lys Ala Pro Gly Leu Thr
        595                 600                 605

Gln Ala Leu Asn Thr Lys Asp Gly Ala Val Met Val Met Ser Tyr Gly
    610                 615                 620

Asn Ser Glu Glu Asp Ser Gln Glu His Thr Gly Ser Gln Leu Arg Ile
625                 630                 635                 640

Ala Ala Tyr Gly Pro His Ala Ala Asn Val Val Gly Leu Thr Asp Gln
                645                 650                 655

Thr Asp Leu Phe Tyr Thr Met Lys Ala Ala Leu Gly Leu Lys Gly Ala
            660                 665                 670

Pro Asp Tyr Lys Asp Asp Asp Asp Lys Gly Ala Pro His His His His
        675                 680                 685

His His
    690

<210> SEQ ID NO 15
<211> LENGTH: 221
<212> TYPE: PRT
<213> ORGANISM: Artificial Sequence
<220> FEATURE:
<223> OTHER INFORMATION: AbD31998 heavy chain

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
                20                  25                  30

Tyr Met Ser Trp Val Arg Gln Ala Pro Gly Gln Gly Leu Glu Trp Met
            35                  40                  45

Gly Trp Ile Asn Pro Tyr Asn Gly Val Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

```
Met Glu Leu Ser Arg Leu Arg Ser Glu Asp Thr Ala Val Tyr Tyr Cys
                85                  90                  95

Ala Arg Gly Leu Gly Ser Gln Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Glu Phe
    210                 215                 220
```

<210> SEQ ID NO 16
<211> LENGTH: 214
<212> TYPE: PRT
<213> ORGANISM: Artificial Sequence
<220> FEATURE:
<223> OTHER INFORMATION: AbD31998 light chain

<400> SEQUENCE: 16

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Tyr
                20                  25                  30

Asn Thr Val Ser Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Trp Asp His Leu
                85                  90                  95

Ser Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
            195                 200                 205

Val Ala Pro Thr Glu Ala
    210
```

<210> SEQ ID NO 17
<211> LENGTH: 5
<212> TYPE: PRT
<213> ORGANISM: Artificial Sequence
<220> FEATURE:
<223> OTHER INFORMATION: AbD31998 - heavy chain CDR1

<400> SEQUENCE: 17

Asn Tyr Tyr Met Ser
1               5

<210> SEQ ID NO 18
<211> LENGTH: 17
<212> TYPE: PRT
<213> ORGANISM: Artificial Sequence
<220> FEATURE:
<223> OTHER INFORMATION: AbD31998 heavy chain CDR2

<400> SEQUENCE: 18

Trp Ile Asn Pro Tyr Asn Gly Val Thr Asn Tyr Ala Gln Lys Phe Gln
1               5                   10                  15

Gly

<210> SEQ ID NO 19
<211> LENGTH: 8
<212> TYPE: PRT
<213> ORGANISM: Artificial Sequence
<220> FEATURE:
<223> OTHER INFORMATION: AbD31998 heavy chain CDR3

<400> SEQUENCE: 19

Gly Leu Gly Ser Gln Phe Asp Tyr
1               5

<210> SEQ ID NO 20
<211> LENGTH: 14
<212> TYPE: PRT
<213> ORGANISM: Artificial Sequence
<220> FEATURE:
<223> OTHER INFORMATION: AbD31998 light chain CDR1

<400> SEQUENCE: 20

Thr Gly Thr Ser Ser Asp Val Gly Lys Tyr Asn Thr Val Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: AbD31998 light chain CDR2

<400> SEQUENCE: 21

Gly Val Ser Lys Arg Pro Ser
1               5

<210> SEQ ID NO 22
<211> LENGTH: 9
<212> TYPE: PRT
<213> ORGANISM: Artificial Sequence
<220> FEATURE:
<223> OTHER INFORMATION: AbD31998 light chain CDR3

<400> SEQUENCE: 22

Gly Ser Trp Asp His Leu Ser Tyr Val
1               5

<210> SEQ ID NO 23
<211> LENGTH: 691
<212> TYPE: PRT
<213> ORGANISM: Artificial Sequence
<220> FEATURE:
<223> OTHER INFORMATION: AbD31999 - Fd chain and tags

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Arg Ile Ser Pro Phe Ser Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Ile Gly Pro Asn Trp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Glu Phe Lys Ala
    210                 215                 220

Glu Met Pro Val Leu Glu Asn Arg Ala Ala Gln Gly Asp Ile Thr Thr
225                 230                 235                 240

Pro Gly Gly Ala Arg Arg Leu Thr Gly Asp Gln Thr Ala Ala Leu Arg
                245                 250                 255

Asp Ser Leu Ser Asp Lys Pro Ala Lys Asn Ile Ile Leu Leu Ile Gly
            260                 265                 270

Asp Gly Met Gly Asp Ser Glu Ile Thr Ala Ala Arg Asn Tyr Ala Glu
        275                 280                 285

Gly Ala Gly Gly Phe Phe Lys Gly Ile Asp Ala Leu Pro Leu Thr Gly
    290                 295                 300

Gln Tyr Thr His Tyr Ala Leu Asn Arg Lys Thr Gly Lys Pro Asp Tyr
305                 310                 315                 320

Val Thr Ser Ser Ala Ala Ser Ala Thr Ala Trp Ser Thr Gly Val Lys
                325                 330                 335

Thr Tyr Asn Gly Ala Leu Gly Val Asp Ile His Glu Lys Asp His Pro
            340                 345                 350

Thr Ile Leu Glu Met Ala Lys Ala Ala Gly Leu Ala Thr Gly Asn Val
        355                 360                 365
```

```
Ser Thr Ala Glu Leu Gln Asp Ala Thr Pro Ala Ala Leu Val Ala His
    370                 375                 380

Val Thr Ser Arg Lys Cys Tyr Gly Pro Ser Ala Thr Ser Glu Lys Cys
385                 390                 395                 400

Pro Gly Asn Ala Leu Glu Lys Gly Gly Lys Gly Ser Ile Thr Glu Gln
                405                 410                 415

Leu Leu Asn Ala Arg Ala Asp Val Thr Leu Gly Gly Gly Ala Lys Thr
                420                 425                 430

Phe Ala Glu Thr Ala Thr Ala Gly Glu Trp Gln Gly Lys Thr Leu Arg
            435                 440                 445

Glu Gln Ala Gln Ala Arg Gly Tyr Gln Leu Val Ser Asp Ala Ala Ser
    450                 455                 460

Leu Asn Ser Val Thr Glu Ala Asn Gln Gln Lys Pro Leu Leu Gly Leu
465                 470                 475                 480

Phe Ala Asp Gly Asn Met Pro Val Arg Trp Leu Gly Pro Lys Ala Thr
                485                 490                 495

Tyr His Gly Asn Ile Asp Lys Pro Ala Val Thr Cys Thr Pro Asn Pro
                500                 505                 510

Gln Arg Asn Asp Ser Val Pro Thr Leu Ala Gln Met Thr Asp Lys Ala
            515                 520                 525

Ile Glu Leu Leu Ser Lys Asn Glu Lys Gly Phe Phe Leu Gln Val Glu
530                 535                 540

Gly Ala Ser Ile Asp Lys Gln Asp His Ala Ala Asn Pro Cys Gly Gln
545                 550                 555                 560

Ile Gly Glu Thr Val Asp Leu Asp Glu Ala Val Gln Arg Ala Leu Glu
                565                 570                 575

Phe Ala Lys Lys Glu Gly Asn Thr Leu Val Ile Val Thr Ala Asp His
            580                 585                 590

Ala His Ala Ser Gln Ile Val Ala Pro Asp Thr Lys Ala Pro Gly Leu
            595                 600                 605

Thr Gln Ala Leu Asn Thr Lys Asp Gly Ala Val Met Val Met Ser Tyr
    610                 615                 620

Gly Asn Ser Glu Glu Asp Ser Gln Glu His Thr Gly Ser Gln Leu Arg
625                 630                 635                 640

Ile Ala Ala Tyr Gly Pro His Ala Ala Asn Val Val Gly Leu Thr Asp
                645                 650                 655

Gln Thr Asp Leu Phe Tyr Thr Met Lys Ala Ala Leu Gly Leu Lys Gly
            660                 665                 670

Ala Pro Asp Tyr Lys Asp Asp Asp Lys Gly Ala Pro His His His His
            675                 680                 685

His His His
    690

<210> SEQ ID NO 24
<211> LENGTH: 222
<212> TYPE: PRT
<213> ORGANISM: Artificial Sequence
<220> FEATURE:
<223> OTHER INFORMATION: AbD31999 heavy chain

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30
```

Tyr Met His Trp Val Arg Gln Ala Pro Gly Gln Gly Leu Glu Trp Met
         35                  40                  45

Gly Arg Ile Ser Pro Phe Ser Gly Asn Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Gly Ile Gly Pro Asn Trp Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Glu Phe
    210                 215                 220

<210> SEQ ID NO 25
<211> LENGTH: 216
<212> TYPE: PRT
<213> ORGANISM: Artificial Sequence
<220> FEATURE:
<223> OTHER INFORMATION: AbD31999 light chain

<400> SEQUENCE: 25

Asp Ile Val Leu Thr Gln Pro Pro Ser Val Ser Gly Ala Pro Gly Gln
1               5                  10                  15

Arg Val Thr Ile Ser Cys Thr Gly Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Tyr Asn Tyr Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Trp Asp Ser His
                 85                  90                  95

Leu Lys Ser Val Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

```
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Ala
    210                 215

<210> SEQ ID NO 26
<211> LENGTH: 5
<212> TYPE: PRT
<213> ORGANISM: Artificial Sequence
<220> FEATURE:
<223> OTHER INFORMATION: AbD31999 heavy chain CDR1

<400> SEQUENCE: 26

Thr Tyr Tyr Met His
1               5

<210> SEQ ID NO 27
<211> LENGTH: 17
<212> TYPE: PRT
<213> ORGANISM: Artificial Sequence
<220> FEATURE:
<223> OTHER INFORMATION: AbD31999 heavy chain CDR2

<400> SEQUENCE: 27

Arg Ile Ser Pro Phe Ser Gly Asn Thr Asn Tyr Ala Gln Lys Phe Gln
1               5                   10                  15
Gly

<210> SEQ ID NO 28
<211> LENGTH: 9
<212> TYPE: PRT
<213> ORGANISM: Artificial Sequence
<220> FEATURE:
<223> OTHER INFORMATION: AbD31999 heavy chain CDR3

<400> SEQUENCE: 28

Gly Ile Gly Pro Asn Trp Phe Asp Tyr
1               5

<210> SEQ ID NO 29
<211> LENGTH: 14
<212> TYPE: PRT
<213> ORGANISM: Artificial Sequence
<220> FEATURE:
<223> OTHER INFORMATION: AbD31999 light chain CDR1

<400> SEQUENCE: 29

Thr Gly Ser Ser Ser Asn Ile Gly Ala Gly Tyr Asp Val His
1               5                   10

<210> SEQ ID NO 30
<211> LENGTH: 7
<212> TYPE: PRT
<213> ORGANISM: Artificial Sequence
<220> FEATURE:
<223> OTHER INFORMATION: AbD31999 - light chain CDR2

<400> SEQUENCE: 30

Tyr Asn Tyr Asn Arg Pro Ser
1               5

<210> SEQ ID NO 31
```

```
<211> LENGTH: 11
<212> TYPE: PRT
<213> ORGANISM: Artificial Sequence
<220> FEATURE:
<223> OTHER INFORMATION: AbD31999 light chain CDR3

<400> SEQUENCE: 31

Gln Ser Trp Asp Ser His Leu Lys Ser Val Val
1               5                   10

<210> SEQ ID NO 32
<211> LENGTH: 20
<212> TYPE: DNA
<213> ORGANISM: Artificial Sequence
<220> FEATURE:
<223> OTHER INFORMATION: CSSV ORF3 F-74 primer

<400> SEQUENCE: 32
ctgaagcgag taggcaacaa                                         20

<210> SEQ ID NO 33
<211> LENGTH: 20
<212> TYPE: DNA
<213> ORGANISM: Artificial Sequence
<220> FEATURE:
<223> OTHER INFORMATION: CSSV ORF3 R-151 primer

<400> SEQUENCE: 33
cagtccaagg gatggactct                                         20

<210> SEQ ID NO 34
<211> LENGTH: 20
<212> TYPE: DNA
<213> ORGANISM: Artificial Sequence
<220> FEATURE:
<223> OTHER INFORMATION: CSSV ORF3 P-129 probe

<400> SEQUENCE: 34
tccatcaggt tgccatggca                                         20

<210> SEQ ID NO 35
<211> LENGTH: 24
<212> TYPE: DNA
<213> ORGANISM: Artificial Sequence
<220> FEATURE:
<223> OTHER INFORMATION: mTcCIR25 forward primer

<400> SEQUENCE: 35
cagataagga aaggtggagt ttgg                                    24

<210> SEQ ID NO 36
<211> LENGTH: 26
<212> TYPE: DNA
<213> ORGANISM: Artificial Sequence
<220> FEATURE:
<223> OTHER INFORMATION: mTcCIR25 reverse primer

<400> SEQUENCE: 36
caagaatgtc tcctacattc actacg                                  26

<210> SEQ ID NO 37
<211> LENGTH: 25
<212> TYPE: DNA
<213> ORGANISM: Artificial Sequence
<220> FEATURE:
<223> OTHER INFORMATION: mTcCIR25 probe
```

-continued

```
<400> SEQUENCE: 37
ttcccgtaag cttcgtccca gatgc                                              25
```